(12) United States Patent
Granoff et al.

(10) Patent No.: US 7,534,444 B2
(45) Date of Patent: May 19, 2009

(54) MOLECULAR MIMETICS OF MENINGOCOCCAL B EPITOPES WHICH ELICIT FUNCTIONALLY ACTIVE ANTIBODIES

(75) Inventors: Dan M. Granoff, Berkeley, CA (US); Gregory Moe, Alameda, CA (US); Rino Rappuoli, Siena (IT)

(73) Assignee: Novattis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 10/121,456

(22) Filed: Apr. 11, 2002

(65) Prior Publication Data

US 2004/0013686 A1 Jan. 22, 2004

Related U.S. Application Data

(60) Provisional application No. 60/284,554, filed on Apr. 17, 2001, provisional application No. 60/326,838, filed on Oct. 3, 2001.

(51) Int. Cl.
*A61K 39/095* (2006.01)
*A61K 39/02* (2006.01)
*A61K 39/38* (2006.01)
*A61K 38/00* (2006.01)
*C07K 14/00* (2006.01)

(52) U.S. Cl. ............. 424/250.1; 424/190.1; 424/234.1; 424/184.1; 514/2; 530/350; 530/300; 530/825

(58) Field of Classification Search .............. 530/300, 530/350, 825; 424/190.1, 250.1, 234.1, 184.1; 514/2
See application file for complete search history.

(56) References Cited

U.S. PATENT DOCUMENTS

| | | | |
|---|---|---|---|
| 4,356,170 A | 10/1982 | Jennings et al. | 424/92 |
| 4,727,136 A | 2/1988 | Jennings et al. | 424/150.1 |
| 4,970,070 A | 11/1990 | Raff | 424/87 |
| 5,128,460 A * | 7/1992 | Piatak et al. | 536/23.6 |
| 5,510,264 A * | 4/1996 | Van Alstyne et al. | 435/339 |
| 5,576,002 A | 11/1996 | Jennings et al. | 424/197.11 |
| 5,683,699 A | 11/1997 | Jennings et al. | 424/197.11 |
| 5,811,102 A | 9/1998 | Jennings et al. | 424/197.11 |
| 5,902,586 A | 5/1999 | Jennings et al. | 424/178.1 |
| 5,969,130 A | 10/1999 | Jennings et al. | 536/29.1 |
| 6,030,619 A | 2/2000 | Granoff et al. | 424/185.1 |
| 6,048,527 A | 4/2000 | Granoff et al. | 424/150.1 |

FOREIGN PATENT DOCUMENTS

| | | |
|---|---|---|
| EP | 0 145 359 A2 | 6/1985 |
| EP | 0 504 202 B1 | 5/1995 |
| WO | WO 90/06696 A2 | 6/1990 |
| WO | WO 91/08772 A1 | 6/1991 |
| WO | WO 96/14086 A1 | 5/1996 |
| WO | WO 98/08543 A1 | 3/1998 |
| WO | WO 99/57280 | * 11/1999 |
| WO | WO 00/50075 | 8/2000 |
| WO | WO 00/66741 | 11/2000 |
| WO | WO 00/66741 A2 | * 11/2000 |
| WO | WO 01/64922 A2 | * 9/2001 |

OTHER PUBLICATIONS

Hoogerhout et al. Infect. Immun. 63: 3473-3478, 1995.*
Christodoulides et al. J. Gen. Microbiol. 139: 1729-1738, 1993.*
Ashton et al., "Protective efficacy of mouse serum to the N-propionyl derivative of meningococcal group B polysaccharide," *Microb. Patheogeneis* 6:455-458 (1989).
Ashton et al., "Immunological properties of monoclonal antibodies to the N-propionyl derivative of group B meningococcal polysaccharide," In: *Neisseria 1990, Achtman M. (Ed.)*. Walter De Gruyter & Co. Berlin pp. 187-191 (1991).
Bartoloni et al., "Immunogenicity of meningococcal B polysaccharide conjugated to tetanus toxoid or CRM197 via adipic acid dihydrazide," *Vaccine* 13(5):463-470 (1995).
Baumann et al., "Comparison of the conformation of the epitope of α(2->8) polysialic acid with its reduced and N-acyl derivatives," *Biochemistry* 32:4007-4013 (1993).
Bitter-Suermann et al., "Monoclonal antibodies to polysialic acid reveal epitope sharing between invasive pathogenic bacteria, differentiating cells and tumor cells," *Immunol. Res.*6:225-237 (1987).
Bowie et al., "Deciphering the message in protein sequences: tolerance to amino acid substitutions," *Science* 247:1306-1310 (1990).
Brisson et al., "Helical Epitope of the Group B Meningococcal α(2->8)-Linked Sialic Acid Polysaccharide," *Biochemistry* 31:4996-5004 (1992).
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell Biology* 111:2129-2138 (1990).
Cross et al., "Evaluation of immunotherapeutic approaches for the potential treatment of infections caused by K1-positive *Escherichia coli*," *J. Infect. Dis.* 147(1):68-76 (1983).
Devi et al., "Binding diversity of monoclonal antibodies to α(2->8) polysialic acid conjugated to outer membrane vesicle via adipic acid dihydrazide," *FEMS Immunol. Med. Microbiol.* 14:211-220 (1996).
Devi et al., "Immunization of juvenile rhesus monkeys with group B Neisseria meningtidis capsular polysaccharide-protein conjugate vaccines," In:*Neisseria:Proc. Ninth Internet. Pathogenic Neisseria Conference FEMS Immunolog. Med. Microbiol.* Evans et al. (Ed.), S.C.C., England pp. 427-429 (1994).

(Continued)

*Primary Examiner*—S. Devi
(74) *Attorney, Agent, or Firm*—Amy Hessler; Otis Littlefield; Robert Gorman

(57) ABSTRACT

Molecular mimetics of a surface-exposed epitope on loop 4 of PorA of *Neisseria meningitidis* serogroup B (MenB) P1.2 serosubtype and antibodies produced against the same are disclosed. Compositions containing such molecular mimetics or the antibodies thereto can be used to prevent MenB disease, as well as for diagnosis of MenB infection.

18 Claims, 7 Drawing Sheets

OTHER PUBLICATIONS

Dubois et al., "A Monoclonal Antibody Against *Meningococcus* Group B Polysaccharides Used to Immunocapture and Quantify Polysialylated NCAM in Tissues and Biological Fluids," *Journal of Immunological Methods* 181:125-135 (1995).

Frasch, Carl E., "Meningococcal Vaccines: Past, Present and Future," *Meningococcal Disease* 245-283 (1995).

Frosch et al., "NZB mouse system for production of monoclonal antibodies to weak bacterial antigens: isolation of an IgG antibody to the polysaccharide capsules of *Escherichia coli* K1 and group B meningococci," *PNAS* 82:1194-1198 (1985).

Fusco et al., "Preclinical Evaluation of a Novel Group B Meningococcal Conjugate Vaccine that Elicits Bactericidal Activity in Both Mice and Nonhuman Primates," *The Journal of Infectious Disease* 175:364-372 (1997).

Granoff et al., "Bactericidal monoclonal antibodies that define unique meningococcal B polysaccharide epitopes that do not cross-react with human polysialic acid," *J. Immunology* 160:5028-5036 (1998).

Granoff et al., "Antibody Responses to the Capsular Polysaccharide of *Neisseria Menignitidis* Serogroup B in Patients With Meningococcal Disease," *Clinical and Diagnostic Laboratory Immunology* 2(5):574-582 (1995).

Gregson et al., "Monoclonal antibodies against meningococcal polysaccharide with cross-reactivity against brain antigens," *Biochem. Soc. Transact.* 13:p. 462 (1985).

Häyrinen et al., "Antibodies to Polysialic Acid and its *N*-Propyl Derivative: Binding Properties and Interaction with Human Embryonal Brain Glycopeptides," *The Journal Of Infectious Diseases* 171:1481-1490 (1995).

Horwell, David C., "The 'Peptoid' Approach to the Design of Non-Peptide, Small Molecule Agonist and Antagonists of Neuropeptides," *TIBTech* 13(4):132-134 (1995).

Hurpin et al., "Bactericidal activity of two $IgG_{2a}$ murine monoclonal antibodies with distinct fine specificities for group B *Neisseria meningitidis* capsular polysaccharide," *Hybridoma* 11(6):677-687 (1992).

Husmann et al., "Immunohistochemical localization of polysialic acid in tissue sections: differential binding to polynucleotides and DNA of a murine IgG and a human IgM monoclonal antibody," *J. Histochem. Cytochem.* 38:209-215 (1990).

Jennings, Harold J., "The Capsular Polysaccharide of Group B *Neisseria meningitidis* as a Vehicle for Vaccine Development," *Microbiol. Immunol.* 10:151-165 (1989).

Jennings et al., "Induction of *Meningococcal* Group B Polysaccharide-Specific IgG Antibodies in Mice by Using an *N*-Propionylated B Polysaccharide-Tetanus Toxoid Conjugate Vaccine," *The J. Of Immunology* 137(5):1708-1713 (1986).

Jennings et al., "*N*-Polysialic Group B Meningococcal Polysaccharide Mimic a Unique Epitope on Group B *Neisseria meningitidis*," *J. Experimental Medicine* 165:1207-1211 (1987).

Jennings et al., "Unique Intermolecular Bactericidal Epitope Involving the Homosialopolysaccharide Capsule on the Cell Surface of Group B *Neisseria meningitidis* and *Escherichia coli* K1," *Journal of Immunology* 142(10):3585-3591 (1989).

Jennings et al., "Immunochemistry of Groups A,B, and C Meningococcal Polysaccharide-Tetanus Toxoid Conjugates," *The Journal of Immunology* 127(3):1011-1018 (1981).

Kabat et al., "A human monoclonal macroglobulin with specificity for $\alpha(2->8)$-linked poly-N-acetyl neuraminic acid, the capsular polysaccharide of group B meningococci and *Escherichia coli* K1, which crossreacts with polynucleotides and with denatured DNA," *J. Exp. Med.* 164:642-654 (1986).

Klebert et al., "Primary structure of the murine monoclonal IgG2a antibody mAb735 against $\alpha(2-8)$ polysialic acid," *Biol. Chem. Hoppe Seyler* 374:993-1000 (1993).

Lazar et al., "Transforming growth factor $\alpha$ mutationof aspartic acid 47 and leucine 48 results in different biological activities," *Molecular and Cellular Biology* 8(3):1247-1252 (1988).

Leinonen et al., "Class-specific antibody response to group B *Neisseria meningitidis* capsular polysaccharide: use of polylysine precoating in an enzyme-linked immunosorbent assay," *Infect. Immun.* 38(3):1203-1207 (1982).

Lifely et al., "Specificity of the immune response to the group B polysaccharide of *Neisseria meningitidis*," *Immunology* 74:490-496 (1991).

Livingston et al., "Extended polysialic acid chains (n>55) in glycoproteins from human neuroblastoma cells," *J. Biol. Chem.* 263:9443-9448 (1988).

Lommatzsch et al., "Outer membrane localization of murein hydrolases: MltA, a third lipoprotein lytic transglycosylase in *Escherichia coli*," *J. Bacteriol.* 179:5465-5470 (1997).

Lucas et al., "Functional Differences in Idiotypically Defined IgG1 Anti-Polysaccharide Antibodies Elicited by Vaccination with *Haemophilus influenzae* Type B Polysaccharide-Protein Conjugates," *The Journal of Immunology* 154:4195-4202 (1995).

Mandrell et al., "Complement-Mediated Bactericidal Activity of Human Antibodies in Poly $\alpha 2 \rightarrow 8$ N-Acetylneuraminic Acid, the Capsular Polysaccharide of *Neisseria meningitidis* Serogroup B," *The Journal of Infectious Diseases* 172:1279-1289 (1995).

Michon et al., "Conformational Differences Between Linear $\alpha(2\rightarrow 8)$-Linked Homosialooligosaccharides and the Epitope of the Group B Meningococcal Polysaccharide," *Biochemistry* 26:8399-8405 (1987).

Moreno et al., "Immunological properties of monoclonal antibodies specific for meningococcal polysacchrides: the protective capacity of IgM antibodies specific for polysacharied group B," *J. Gen. Microbiol.* 129:2451-2456 (1983).

Pizza et al., "Identification of vaccine candidates against serogroup B Meningococcus by whole-genome sequencing," *Science* 287:1816-1820 (2000).

Pon et al., "N-propionylated group B meningococcal polysaccharide mimics a unique bactericidal capsular epitope in group B *Neisseria meningitidis*," *J. Exp. Med.* 185:1929-1938 (1997).

Poolman, Jan T., "Development of a Meningococcal Vaccine," *Infectious Agents and Disease* 4:13-28 (1995).

Raff et al., "Human monoclonal antibody with protective activity for *Escherichia coli* K1 and *Neisseria meningitidis* group B infections," *J. Infect. Dis.* 157(1):118-126 (1988).

Rougon et al., "A monoclonal antibody against meningococcus group B polysaccharides distinguishes embryonic from adult N-CAM," *J. Cell. Biol.* 103:2429-2437 (1986).

Sato et al., "Characterization of the antigenic specificity of four different anti-$\alpha(2->8)$-linked polysialic acid) antibodies using lipid-conjugated oligo/polysialic acids," *J. Biol. Chem.* 270:18923-18928 (1995).

Saukkonen et al., "Antibodies to the capsular polysaccharide of *Neisseria meningitidis* group B or *E. coli* K1 bind to the brains of infant rats in vitro but not in vivo," *Microbiol. Pathogenesis* 1:101-105 (1986).

Tettelin et al., "Complete genome sequence of *Neisseria meningitidis* serogroup B strain MC58," *Science* 287:1809-1815 (2000).

Tome et al., "Comparison of immunoreactivity between two different monoclonal antibodies recognizing peptide and polysialic acid chain epitopes on the neural cell adhesion molecule in normal tissues and lung tumors," *Acta Pathol. Jpn.* 43:168-175 (1993).

Vaesen et al., "Primary structure of the murine monoclonal IgG2a antibody mAb735 against $\alpha(2-8)$ polysialic acid," *Biol. Chem. Hoppe-Seyler* 372:451-453 (1993).

Westerink et al., "Development and Characterization of an Anti-Idiotype Antibody to the Capsular Polysaccharide of *Neisseria mengingitidis* Serogroup C," *Infection and Immunity* 56(5):1120-1127 (1988).

DataBase WPI., "Novel Strain of *Neisseria meningitidis* Group Useful Produce Capsule Polysaccharide Protein Complex," XP002053202, Jan. 30, 1992.

Jansen et al., "Immunogenicity of an in vitro folded outer membrane protein PorA of *Neisseria meningitidis*," *FEMS Immunol. Med. Microbiol.* 27, 227-33, Mar. 2000.

Granoff et al., "A highly conserved Neisserial lipoprotein that elicits protective antibody to N. meningitidis serogroup B strains by mimicking a surface-exposed epitope on loop 4 of PorA," *Ped. Res. 49,*

256A, Apr. 2001 and *Ann. Meeting of the Pediatric Academic Societies*, Baltimore MD Apr. 28-May 1, 2001.

Granoff et al., "A novel mimetic antigen eliciting protective antibody to *Neisseria meningitidis*," *J. Immunol. 167*, 6487-96, Dec. 1, 2001.

AAY75656 Mar. 12, 2000, Fraser et al.: "*Neisseria gonorrheae* ORF 919 protein sequence ID No. 2790" XP002348584.

\* cited by examiner

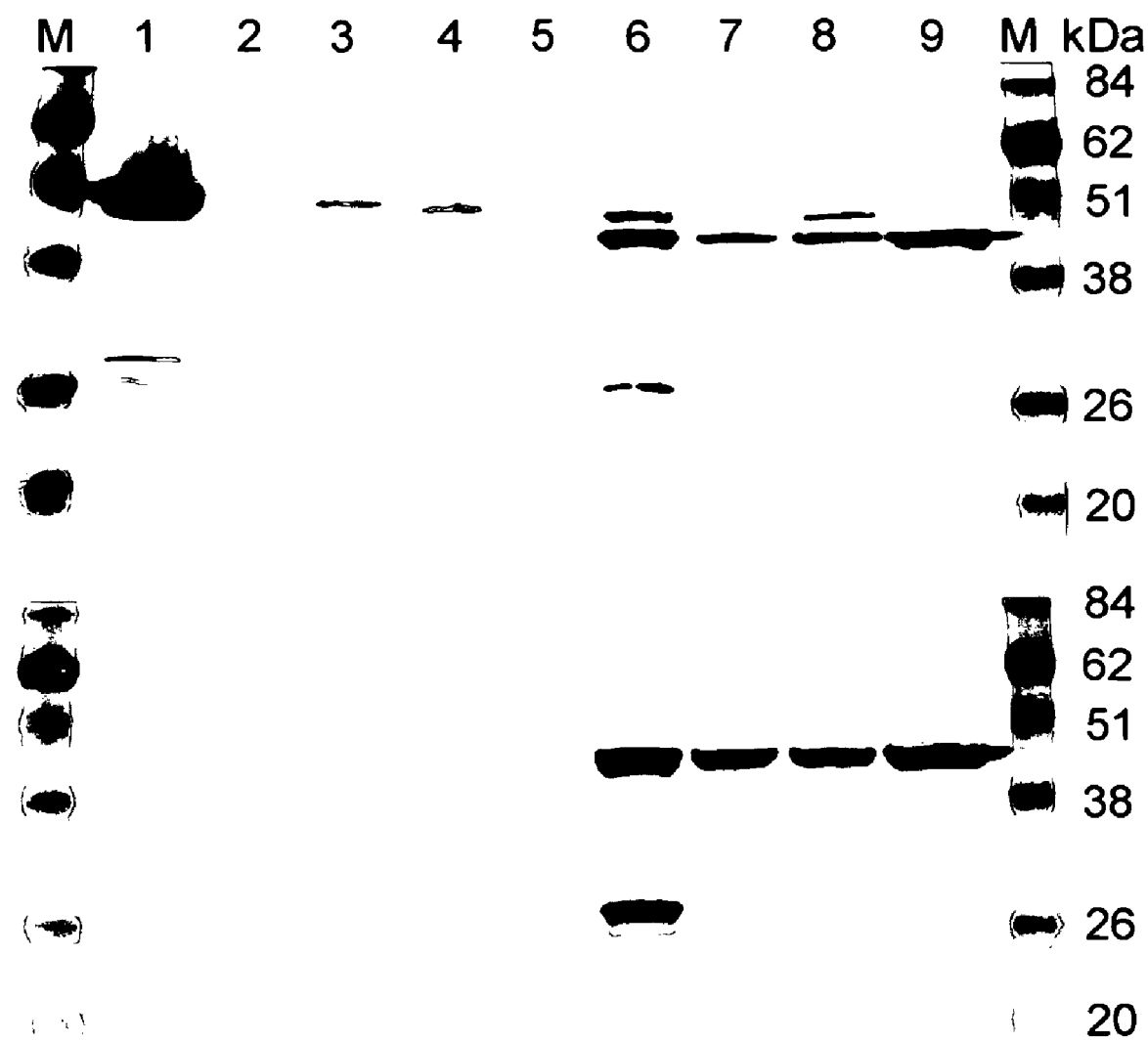

| | | | | |
|---|---|---|---|---|
| 1 | MKKYLFRAAL | CGIAAAILAA | CQSKSIQTFP | QPDTSVINGP | DRPVGIPDPA |
| 51 | GTTVGGGGAV | YTVVPHLSLP | HWAAQDFAKS | LQSFRLGCAN | LKNRQGWQDV |
| 101 | CAQAFQTPVH | SVQAKQFFER | YFTPWQVAGN | GSLAGTVTGY | YEPVLKGDDR |
| 151 | RTAQARFPIY | GIPDDFISVP | LPAGLRSGKA | LVRIRQTGKN | SGTIDNTGGT |
| 201 | HTADLSQFPI | TARTTAIKGR | FEGSRFLPYH | TRNQINGGAL | DGKAPILGYA |
| 251 | EDPVELFFMH | IQGSGRLKTP | SGKYIRIGYA | DKNEHPYVSI | GRYMADKGYL |
| 301 | KLGQTSMQGI | KAYMQQNPQR | LAEVLGQNPS | YIFFRELTGS | SNDGPVGALG |
| 351 | TPLMGEYAGA | VDRHYITLGA | PLFVATAHPV | TRKALNRLIM | AQDTGSAIKG |
| 401 | AVRVDYFWGY | GDEAGELAGK | QKTTGYVWQL | LPNGMKPEYR | P |

FIG. 3

```
                       SEQUENCE LISTING

<160> NUMBER OF SEQ ID NOS: 55

<210> SEQ ID NO 1
<211> LENGTH: 441
<212> TYPE: PRT
<213> ORGANISM: Artificial Sequence
<220> FEATURE:
<223> OTHER INFORMATION: Description of Artificial Sequence: exemplary
      GNA33 sequence

<400> SEQUENCE: 1

Met Lys Lys Tyr Leu Phe Arg Ala Ala Leu Cys Gly Ile Ala Ala Ala
  1               5                  10                  15

Ile Leu Ala Ala Cys Gln Ser Lys Ser Ile Gln Thr Phe Pro Gln Pro
                 20                  25                  30

Asp Thr Ser Val Ile Asn Gly Pro Asp Arg Pro Val Gly Ile Pro Asp
             35                  40                  45

Pro Ala Gly Thr Thr Val Gly Gly Gly Ala Val Tyr Thr Val Val
         50                  55                  60

Pro His Leu Ser Leu Pro His Trp Ala Ala Gln Asp Phe Ala Lys Ser
 65                  70                  75                  80

Leu Gln Ser Phe Arg Leu Gly Cys Ala Asn Leu Lys Asn Arg Gln Gly
                 85                  90                  95

Trp Gln Asp Val Cys Ala Gln Ala Phe Gln Thr Pro Val His Ser Val
                100                 105                 110

Gln Ala Lys Gln Phe Phe Glu Arg Tyr Phe Thr Pro Trp Gln Val Ala
            115                 120                 125
```

```
Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Gln Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ala Tyr Met Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: GNA33
      polypeptide

<400> SEQUENCE: 2

Phe Gln Thr Pro Val
  1               5

<210> SEQ ID NO 3
<211> LENGTH: 7
<212> TYPE: PRT
<213> ORGANISM: Artificial Sequence
```

```
<220> FEATURE:
<223> OTHER INFORMATION: Description of Artificial Sequence: GNA33
      polypeptide

<400> SEQUENCE: 3

Phe Gln Thr Pro Val His Ser
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: GNA33
      polypeptide

<400> SEQUENCE: 4

Ala Phe Gln Thr Pro Val His Ser
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: GNA33
      polypeptide

<400> SEQUENCE: 5

Gln Ala Phe Gln Thr Pro Val His Ser
 1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: GNA33
      polypeptide

<400> SEQUENCE: 6

Ala Gln Ala Phe Gln Thr Pro Val His Ser
 1               5                  10

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: GNA33
      polypeptide

<400> SEQUENCE: 7

Ala Gln Ala Phe Gln Thr Pro Val His
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: GNA33
      polypeptide

<400> SEQUENCE: 8

Ala Gln Ala Phe Gln Thr Pro Val
 1               5
```

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: GNA33
      polypeptide

<400> SEQUENCE: 9

Gln Ala Phe Gln Thr Pro Val His Ser Phe
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: GNA33
      polypeptide

<400> SEQUENCE: 10

Ala Phe Gln Thr Pro Val His Ser Phe Gln
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: GNA33
      polypeptide

<400> SEQUENCE: 11

Phe Gln Thr Pro Val His Ser Phe Gln Ala
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: GNA33
      polypeptide

<400> SEQUENCE: 12

Gln Thr Pro Val His Ser Phe Gln Ala Lys
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: GNA33
      polypeptide

<400> SEQUENCE: 13

Val Ser Ala Gln Ala Phe Gln Thr Pro Val
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: GNA33
      polypeptide -continued

```
<400> SEQUENCE: 14

Ser Ala Gln Ala Phe Gln Thr Pro Val His
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Loop 4 of
      PorA P1.2^A

<400> SEQUENCE: 15

Ala His Phe Val Gln Gln Thr Pro Gln Ser
 1               5                  10

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: hexapeptide

<400> SEQUENCE: 16

Gln Thr Pro Lys Ser Gln
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: hexapeptide

<400> SEQUENCE: 17

Gln Thr Pro Gln Ser Gln
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: hexapeptide

<400> SEQUENCE: 18

Asn Lys Gln Asn Gln Arg
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: hexapeptide

<400> SEQUENCE: 19

Asn Lys Gln Asn Gln Pro
 1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: sequence in
      error
```

```
<400> SEQUENCE: 20

Gln Thr Pro Glu
 1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: correct
      sequence

<400> SEQUENCE: 21

Gln Thr Pro Gln
 1

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Loop 4 of
      PorA P1.2^A

<400> SEQUENCE: 22

Thr Pro Ala His Phe Val Gln Gln Thr Pro
 1               5                  10

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: PorA P1.2
      peptide

<400> SEQUENCE: 23

Phe Val Gln Gln Thr Pro
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: segment

<400> SEQUENCE: 24

Phe Val Gln Gln Thr Pro Lys
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: segment

<400> SEQUENCE: 25

Phe Val Gln Gln Thr Pro Gln
 1               5

<210> SEQ ID NO 26
<211> LENGTH: 39
<212> TYPE: DNA
<213> ORGANISM: Artificial Sequence
```

-continued

<220> FEATURE:
<223> OTHER INFORMATION: Description of Artificial Sequence: U33 FOR

<400> SEQUENCE: 26
gctctagaga tgagtcgaac acaatgaaca atgtcctga                39

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: U33REV

<400> SEQUENCE: 27
tcccccgggc tcttgctttg gcaggcggcg a                31

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: D33FOR

<400> SEQUENCE: 28
tcccccgggc acgggatatg tgtggc                26

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: D33REV

<400> SEQUENCE: 29
cccgctcgag agtagggaca accgg                25

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: primer F33

<400> SEQUENCE: 30
gctctagagg gcgacgacag gcgg                24

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: primer R33

<400> SEQUENCE: 31
cccgctcgag ttacgggcgg tattcgg                27

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: strain
    M3735

<400> SEQUENCE: 32

His Phe Val Gln Gln Thr Pro Lys Ser Gln Pro Thr Leu Val Pro

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: strain
      BZ232

<400> SEQUENCE: 33

His Phe Val Gln Gln Thr Pro Gln Ser Gln Pro Thr Leu Val Pro
 1               5                  10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: strain BZ83

<400> SEQUENCE: 34

His Phe Val Gln Asn Lys Gln Asn Gln Arg Pro Thr Leu Val Pro
 1               5                  10                  15

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: GNA33^A

<400> SEQUENCE: 35

Gln Asp Val Ser Ala Gln Ala Phe Gln Thr
 1               5                  10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: GNA33^A

<400> SEQUENCE: 36

Thr Pro Val His Ser Phe Gln Ala Lys Gln
 1               5                  10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Loop 4 of
      PorA P1.2^A

<400> SEQUENCE: 37

Tyr Thr Pro Ala His Phe Val Gln Gln Thr
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Loop 4 of
      PorA P1.2^A

<400> SEQUENCE: 38

```
Pro Ala His Phe Val Gln Gln Thr Pro Gln
  1               5                  10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Loop 4 of
      PorA P1.2^A

<400> SEQUENCE: 39

His Phe Val Gln Gln Thr Pro Gln Ser Gln
  1               5                  10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Loop 4 of
      PorA P1.2^A

<400> SEQUENCE: 40

Phe Val Gln Gln Thr Pro Gln Ser Gln Pro
  1               5                  10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Loop 4 of
      PorA P1.2^A

<400> SEQUENCE: 41

Val Gln Gln Thr Pro Gln Ser Gln Pro Thr
  1               5                  10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Loop 4 of
      PorA P1.2^A

<400> SEQUENCE: 42

Gln Gln Thr Pro Gln Ser Gln Pro Thr Leu
  1               5                  10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Loop 4 of
      PorA P1.2^A

<400> SEQUENCE: 43

Gln Thr Pro Gln Ser Gln Pro Thr Leu Val
  1               5                  10

<210> SEQ ID NO 44
<211> LENGTH: 9
<212> TYPE: PRT
<213> ORGANISM: Artificial Sequence
```

```
<220> FEATURE:
<223> OTHER INFORMATION: Description of Artificial Sequence: Loop 4 of
      PorA P1.2^A

<400> SEQUENCE: 44

Thr Pro Gln Ser Gln Pro Thr Val Pro
 1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: 10-mer
      Peptide

<400> SEQUENCE: 45

Pro Gly His Phe Val Gln Gln Thr Pro Gln
 1               5                  10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: 10-mer
      Peptide

<400> SEQUENCE: 46

Pro Ala Ala Phe Val Gln Gln Thr Pro Gln
 1               5                  10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: 10-mer
      Peptide

<400> SEQUENCE: 47

Pro Ala His Ala Val Gln Gln Thr Pro Gln
 1               5                  10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: 10-mer
      Peptide

<400> SEQUENCE: 48

Pro Ala His Phe Ala Gln Gln Thr Pro Gln
 1               5                  10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: 10-mer
      Peptide

<400> SEQUENCE: 49

Pro Ala His Phe Val Ala Gln Thr Pro Gln
 1               5                  10
```

```
<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: 10-mer
      Peptide

<400> SEQUENCE: 50

Pro Ala His Phe Val Gln Ala Thr Pro Gln
 1               5                  10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: 10-mer
      Peptide

<400> SEQUENCE: 51

Pro Ala His Phe Val Gln Gln Ala Pro Gln
 1               5                  10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: 10-mer
      Peptide

<400> SEQUENCE: 52

Pro Ala His Phe Val Gln Gln Thr Ala Gln
 1               5                  10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: 10-mer
      Peptide

<400> SEQUENCE: 53

Pro Ala His Phe Val Gln Gln Thr Pro Ala
 1               5                  10

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Consensus
      Peptide

<400> SEQUENCE: 54

Phe Val Gln Gln Thr Pro Ala
 1               5

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: GNA33
      polypeptide
```

-continued

```
<400> SEQUENCE: 55

Asp Val Ser Ala Gln Ala Phe Gln Thr Pro
  1               5                  10
```

MOLECULAR MIMETICS OF MENINGOCOCCAL B EPITOPES WHICH ELICIT FUNCTIONALLY ACTIVE ANTIBODIES

CROSS-REFERENCE TO RELATED APPLICATION

This application claims the benefit under 35 USC §119(e)(1) of provisional patent application Ser. Nos. 60/284,554, filed Apr. 17, 2001, and 60/326,838, filed Oct. 3, 2001 which applications are incorporated herein by reference in their entireties.

TECHNICAL FIELD

The present invention pertains generally to bacterial pathogens. In particular, the invention relates to molecular mimetics of a surface-exposed epitope on loop 4 of PorA of *Neisseria meningitidis* serogroup B (MenB) P1.2 serosubtype and antibodies produced against the same.

BACKGROUND OF THE INVENTION

*Neisseria meningitidis* is a causative agent of bacterial meningitis and sepsis. Meningococci are divided into serological groups based on the immunological characteristics of capsular and cell wall antigens. Currently recognized serogroups include A, B, C, W-135, X, Y, Z and 29E. The polysaccharides responsible for the serogroup specificity have been purified from several of these groups, including A, B, C, W-135 and Y.

*N. meningitidis* serogroup B (termed "MenB" or "NmB" herein) accounts for a large percentage of bacterial meningitis in infants and children residing in the U.S. and Europe. The organism also causes fatal sepsis in young adults. In adolescents, experimental MenB vaccines consisting of outer membrane protein (OMP) vesicles are somewhat protective. However, no protection has been observed in vaccinated infants, the age group at greatest risk of disease. Additionally, OMP vaccines are serotype- and subtype-specific, and the dominant MenB strains are subject to both geographic and temporal variation, limiting the usefulness of such vaccines.

Effective capsular polysaccharide-based vaccines have been developed against meningococcal disease caused by serogroups A, C, Y and W135. However, similar attempts to develop a MenB polysaccharide vaccine have failed due to the poor immunogenicity of the capsular MenB polysaccharide (termed "MenB PS" herein). MenB PS is a homopolymer of (N-acetyl ($\alpha$ 2->8) neuraminic acid. *Escherichia coli* K1 has the identical capsular polysaccharide. Antibodies elicited by MenB PS cross-react with host polysialic acid (PSA). PSA is abundantly expressed in fetal and newborn tissue, especially on neural cell adhesion molecules ("NCAMs") found in brain tissue. PSA is also found to a lesser extent in adult tissues including in kidney, heart and the olfactory nerve. Thus, most anti-MenB PS antibodies are also autoantibodies. Such antibodies therefore have the potential to adversely affect fetal development, or to lead to autoimmune disease.

MenB PS derivatives have been prepared in an attempt to circumvent the poor immunogenicity of MenB PS. For example, $C_3$-$C_8$ N-acyl-substituted MenB PS derivatives have been described. See, EP Publication No. 504,202 B, to Jennings et al. Similarly, U.S. Pat. No. 4,727,136 to Jennings et al. describes an N-propionylated MenB PS molecule, termed "NPr-MenB PS" herein. Mice immunized with NPr-MenB PS glycoconjugates were reported to elicit high titers of IgG antibodies. Jennings et al. (1986) *J. Immunol.* 137:1708. In rabbits, two distinct populations of antibodies, purportedly associated with two different epitopes, one shared by native MenB PS and one unshared, were produced using the derivative. Bactericidal activity was found in the antibody population that did not cross react with MenB PS. Jennings et al. (1987) *J. Exp. Med.* 165:1207. The identity of the bacterial surface epitope(s) reacting with the protective antibodies elicited by this conjugate remains unknown. Also, because a subset of antibodies elicited by this vaccine have autoreactivity with host polysialic acid (Granoff et al. (1998) *J. Immunol.* 160:5028) the safety of this vaccine in humans remains uncertain.

Despite these attempts, conventional approaches have failed to identify antigens that are safe and capable of conferring broad protection against MenB infection.

There has been considerable interest in using molecular mimetic antigens to elicit protective immune responses to various pathogens, as well as for the treatment of cancer and autoimmune diseases. This approach to vaccine development for the prevention of infectious diseases has the greatest utility when the nominal antigen is toxic or difficult to purify, or when it is desirable to direct the immune response to a limited number of epitopes. Nevertheless, there are relatively few studies that report success of a mimetic vaccine in eliciting protective antibodies to a pathogen.

A number of functionally active antibodies directed against MenB PS derivatives have been described in U.S. Pat. No. 6,048,527. These antibodies do not cross-react, or are minimally cross-reactive with host tissues, and thus pose minimal risk of evoking autoimmune disease. U.S. Pat. No. 6,030,619 describes molecular mimetics of unique epitopes of MenB PS identified using these antibodies. However, the discovery of peptide mimetics of other MenB antigens remains of considerable interest.

The complete genomic sequence of MenB, strain MC58, has been described. Tettelin et al., *Science* (2000) 287:1809. Several proteins that elicited serum bactericidal antibody responses have been identified by whole genome sequencing. These proteins have conserved sequences and appear to be surface-exposed on encapsulated MenB strains. Pizza et al., *Science* (2000) 287:1816. One of these proteins is GNA33 (genome derived antigen). GNA33 is a lipoprotein and the predicted amino acid sequence shows homology with a membrane-bound lytic murein transglycosylase (MltA) from *E. coli* and *Synechocystis* sp. Lommatzsch et al., *J. Bacteriol.* (1997) 179:5465-5470. GNA33 is highly conserved among *Neisseria meningitidis*. Pizza et al., *Science* (2000) 287:1816. Mice immunized with recombinant GNA33 developed high serum bactericidal antibody titers measured against encapsulated MenB strain 2996. The magnitude of the antibody response was similar to that of control animals immunized with OMP vesicles prepared from strain 2996. However, the mechanism by which GNA33 elicits protective antibody was not identified, nor was the breadth of the protective response to different MenB strains.

It is readily apparent that the production of a safe and effective vaccine against MenB would be particularly desirable.

SUMMARY OF THE INVENTION

The present invention is based on the unexpected discovery that GNA33 elicits protective antibodies to MenB by mimicking a surface-exposed epitope on loop 4 of PorA of strains with the P1.2 serosubtype. The functional activity of such antibodies has been assessed as described herein, using in vitro and in vivo functional assays that predict the ability of molecular agents to protect against meningococcal disease in humans.

Accordingly, in one embodiment, the subject invention relates to GNA33 peptides which include epitopes useful for the production of antibodies that demonstrate functional activity against MenB bacteria. The peptides include less than the full-length GNA33 sequence. In particularly preferred embodiments, the peptides include the amino acid sequence QTP and, optionally, additional flanking sequences preceding or following the QTP sequence, preferably 1-50 or more amino acids but less than the full-length sequence, such as 1-3, 1-5, or 1-10, or 1-25, or any integer between these ranges, occurring either C- or N-terminally to the QTP sequence. An exemplary GNA33 sequence is shown in FIG. 3 (SEQ ID NO:1). The QTP occurs at positions 106-108 of FIG. 3. It is to be understood that the sequence is not limited to the sequences flanking QTP as shown in FIG. 3, as the various MenB strains, such as those described herein, have different flanking sequences. The sequences of the PorA region in various strains are known and several are shown in Table 2.

In certain embodiments, the GNA33 peptide comprises an amino acid sequence selected from the group consisting of FQTPV (SEQ ID NO:2), FQTPVHS (SEQ ID NO:3), AFQTPVHS (SEQ ID NO:4), QAFQTPVHS (SEQ ID NO:5), AQAFQTPVHS (SEQ ID NO:6), AQAFQTPVH (SEQ ID NO:7), AQAFQTPV (SEQ ID NO:8), QAFQTPVHSF (SEQ ID NO:9), AFQTPVHSFQ (SEQ ID NO: 10), FQTPVHSFQA (SEQ ID NO: 11), QTPVHSFQAK (SEQ ID NO: 12), DVSAQAFQTP [(SEQ ID NO: 12)](SEQ ID NO:55), VSAQAFQTPV (SEQ ID NO: 13) and SAQAFQTPVH (SEQ ID NO: 14).

In other embodiments, the subject invention is directed to the use of GNA33 polypeptides as carriers to insert other epitopes of serologically different outer membrane proteins, as well as a general carrier.

In another embodiment, the invention is directed to polynucleotides encoding these peptides, as well as recombinant vectors including the polynucleotides, host cells comprising the vectors and methods of recombinantly producing the peptides.

In yet other embodiments, the invention relates to antibodies directed against GNA33 epitopes, wherein the antibodies are capable of being bound by GNA33 epitopes and/or demonstrate functional activity against MenB bacteria. As explained further below, an antibody displays functional activity against a MenB organism when the antibody molecule exhibits complement-mediated bactericidal activity and/or opsonic activity against MenB as determined using the assays described herein. Representative GNA33 epitopes include QTP, FQTPV (SEQ ID NO:2), FQTPVHS (SEQ ID NO:3), AFQTPVHS (SEQ ID NO:4), QAFQTPVHS (SEQ ID NO:5), AQAFQTPVHS (SEQ ID NO:6), AQAFQTPVH (SEQ ID NO:7), AQAFQTPV (SEQ ID NO:8), QAFQTPVHSF (SEQ ID NO:9), AFQTPVHSFQ (SEQ ID NO: 10), FQTPVHSFQA (SEQ ID NO: 11), QTPVHSFQAK (SEQ ID NO:12), DVSAQAFQTP [(SEQ ID NO: 12)](SEQ ID NO:55), VSAQAFQTPV (SEQ ID NO: 13) and SAQAFQTPVH (SEQ ID NO: 14).

Another embodiment of the invention relates to monoclonal antibodies directed against GNA33 epitopes, and hybridomas producing those monoclonal antibodies. Preferably, the monoclonal antibodies display functional activity against a MenB organism.

Still further embodiments of the subject invention are related to methods for isolating further molecular mimetics of epitopes of MenB and the molecular mimetics identified using the methods. The methods comprise:

(a) providing a population of molecules including a putative molecular mimetic of an epitope of MenB;

(b) contacting the population of molecules with the antibodies described herein under conditions that allow immunological binding between the antibody and the molecular mimetic, if present, to provide a complex; and (c) separating the complexes from non-bound molecules.

In another embodiment, the subject invention is directed to a composition comprising GNA33, or a peptide of GNA33 comprising an epitope as described above, in combination with a pharmaceutically acceptable excipient.

In yet another embodiment, the invention is directed to a composition comprising an antibody directed against a GNA33 polypeptide in combination with a pharmaceutically acceptable excipient.

In another embodiment, the invention is directed to a method of eliciting an immune response against *Neisseria meningitidis* serogroup B in a mammalian subject, comprising administering a GNA33 peptide as described above to the subject.

In another embodiment, the subject invention is directed to a method for treating or preventing MenB disease in a mammalian subject comprising administering an effective amount of the above compositions to the subject.

In another embodiment, the invention is directed to a method for detecting *Neisseria meningitidis* serogroup B antibodies in a biological sample comprising:

(a) providing a biological sample;

(b) reacting said biological sample with a GNA33 polypeptide under conditions which allow *Neisseria meningitidis* serogroup B antibodies, when present in the biological sample, to bind to the GNA33 polypeptide to form an antibody/GNA33 polypeptide complex; and (c) detecting the presence or absence of the complex thereby detecting the presence or absence of *Neisseria meningitidis* serogroup B antibodies in the sample.

Representative GNA33 polypeptides include a GNA33 peptide that comprises an amino acid sequence selected from the group consisting of QTP, FQTPV (SEQ ID NO:2), FQTPVHS (SEQ ID NO:3), AFQTPVHS (SEQ ID NO:4), QAFQTPVHS (SEQ ID NO:5), AQAFQTPVHS (SEQ ID NO:6), AQAFQTPVH (SEQ ID NO:7), AQAFQTPV (SEQ ID NO:8), QAFQTPVHSF (SEQ ID NO:9), AFQTPVHSFQ (SEQ ID NO: 10), FQTPVHSFQA (SEQ ID NO: 11), QTPVHSFQAK (SEQ ID NO: 12), DVSAQAFQTP [(SEQ ID NO: 12)] (SEQ ID NO:55), VSAQAFQTPV (SEQ ID NO: 13) and SAQAFQTPVH (SEQ ID NO: 14).

These and other embodiments of the present invention will readily occur to those of ordinary skill in the art in view of the disclosure herein.

BRIEF DESCRIPTION OF THE FIGURES

FIG. 1A shows binding of polyclonal anti-GNA33 antisera and control mAbs to live encapsulated NmB strains 2996 M3735, M4207, and MC58 as determined by indirect fluorescence flow cytometry. The control mAbs and antisera include an anti-serogroup B capsular-specific murine mAb (SEAM 12, Granoff et al., *J. Immunol.* (1998) 160:5028-5036), an *N. meningitidis* serosubtype mAb anti-PorA P1.2, and polyclonal antisera from mice immunized with *E. coli* outer membrane vesicles. FIG. 1B shows binding of anti-GNA33 mAb 25 and control mAbs to NmB strains M3735, M4207, and MC58. The murine control mAbs included a mAb having an irrelevant specificity (VIG10), and the same anticapsular and anti-PorA P1.2 mAbs described above for FIG. 1A.

FIGS. 2A-2B show a western blot of total membrane fractions prepared from different MenB strains and resolved by SDS-PAGE. FIG. 2A shows reactivity with anti-GNA33 mAb 25. Lane 1. rGNA33. Lane 2. Total protein prepared from control E. coli cells. Lanes 3, 4 and 5, respectively: total protein prepared from MenB strains NG3/88 (P1.1), MC58 (P1.7,16), and a mutant of MC58 in which the gene encoding GNA33 has been inactivated (MC58ΔGNA33). Lanes 6, 7, 8 and 9: Total protein from MenB strains BZ232, BZ232ΔGNA33, NMB and NMBΔGNA33, respectively. All four strains are serosubtype P1.5,2. FIG. 2B shows a western blot of the same protein samples as described for FIG. 2A but using the anti-PorA P1.2 mAb as the primary detecting antibody.

FIG. 3 (SEQ ID NO:1) shows the full-length amino acid sequence of a representative GNA33 polypeptide. The underlined amino acids occurring at positions 1-21 correspond to a leader sequence.

FIG. 4 shows binding of anti-GNA33 mAb25 to progressively smaller peptides corresponding to segments from (A) GNA33 and (B) PorA P1.2 (Strain 2996). The respective peptides shown were identified from mapping studies with overlapping 10 mer peptides prepared form each protein and shown to contain an epitope recognized by mAb 25.

FIG. 5A shows concentration-dependent binding of anti-GNA33 mAb 25 to strains 8047 ($BC_{50}$=15 μg/ml with human complement) and BZ232 ($BC_{50}$>150 μg/ml with human complement). Both strains were susceptible to bacteriolysis when tested with rabbit (see text). FIG. 5B shows concentration-dependent anti-GNA33 binding to stains M986 (Por A $VR_2$ type P1.2) and M5682 (PorA $VR_2$ type P1.2), as compared to strain 8047 (PorA $VR_2$ type P1.2-2). M986 was resistant to anti-GNA33 bacteriolysis (human or rabbit), M5682 was susceptible (rabbit complement), and strain 8047 was susceptible (human or rabbit).

DETAILED DESCRIPTION OF THE INVENTION

Figure 1A:
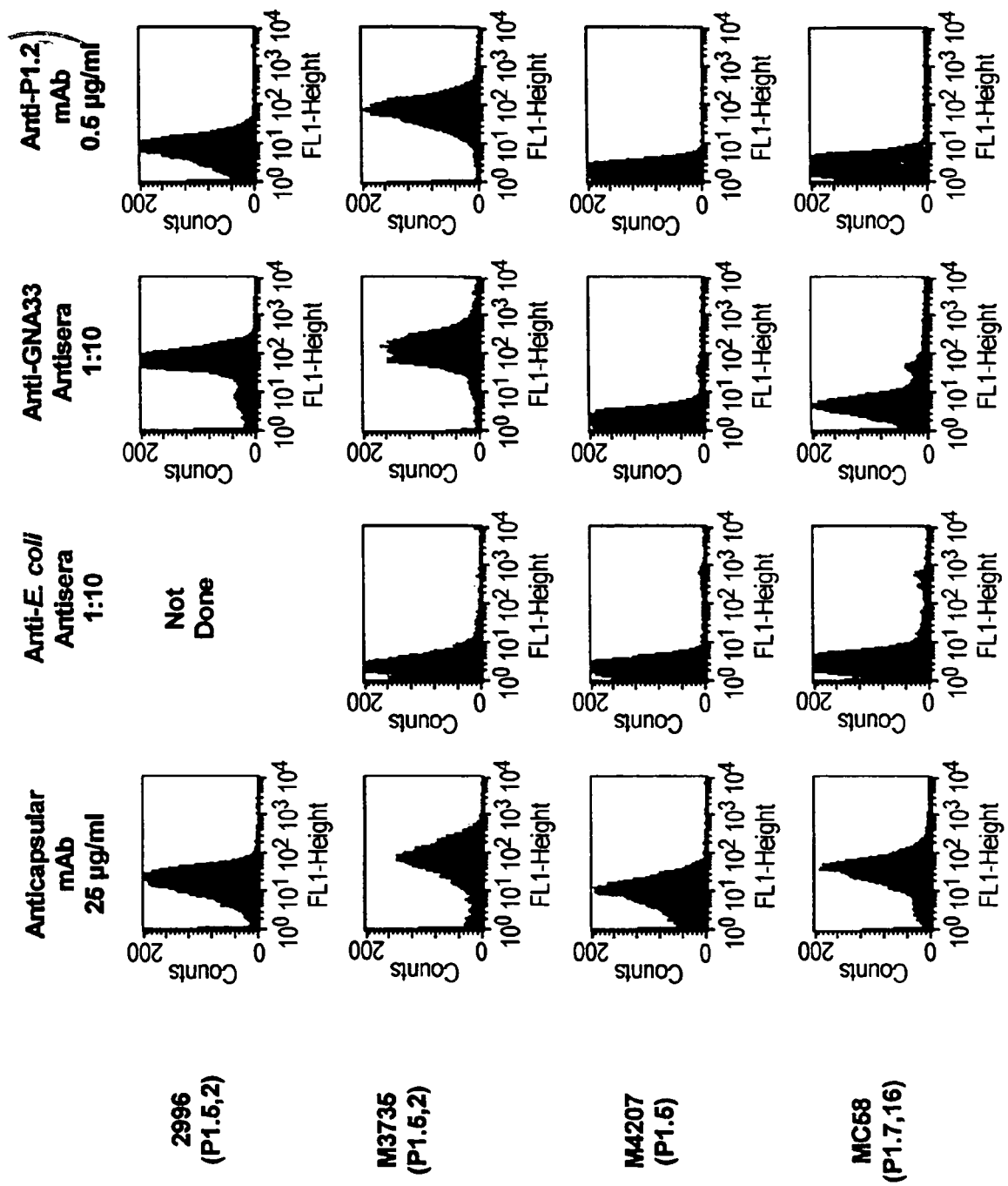
FIGS. 1A-1B show the binding of anti-GNA33 antisera (1A) and antibodies to the surface of live encapsulated NmB strains.

The practice of the present invention will employ, unless otherwise indicated, conventional methods of immunology, microbiology, and molecular biology within the skill of the art. Such techniques are explained fully in the literature. See, e.g., Sambrook, et al. *Molecular Cloning: A Laboratory Manual* (2nd Edition, 1989); Sambrook and Russell, *Molecular Cloning: A Laboratory Manual* (2001); Morrison and Boyd, *Organic Chemistry* (3rd Edition 1973); Carey and Sundberg, *Advanced Organic Chemistry* (2nd Edition, 1985); Smith, M. B., *Organic Synthesis* (1994); Perbal, A *Practical Guide to Molecular Cloning* (1984); and *Handbook of Experimental Immunology*, Vols. I-IV (D. M. Weir and C. C. Blackwell eds., 1986, Blackwell Scientific Publications).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

I. Definitions

In describing the present invention, the following terms will be employed, and are intended to be defined as indicated below.

By "GNA33 polypeptide" is meant a polypeptide derived from the GNA33 protein which is capable of eliciting an immunological response against MenB, such as the production of antibodies which demonstrate functional activity against MenB bacteria, as defined below. The term may be used to refer to an individual macromolecule or to a homogeneous or heterogeneous population of antigenic macromolecules derived from GNA33. For purposes of the present invention, a GNA33 polypeptide may be derived from any of the various known MenB strains. The GNA33 sequence for strain 2996 is shown in FIG. 3 (SEQ ID NO:1). However, a number of GNA33 sequences from other MenB strains are known. See, e.g., GenBank accession nos. C81244, B82023, AF226395, AF226392, AF226390, AF226403, AF226413, AF226412, AF226387, AF226409, AF22641, AF226397, AF226389, AF226393, AF226416, AF226414, AF226402, AF226404, AF235145, AF235144, AF235143, *Neisseria meningitidis*; E83491, *Pseudomonas aeruginosa* (strain PAO1); AF300471, *Zymomonas mobilis*; AAK85834, *Agrobacterium tumefaciens*; CAC41396, *Sinorhizobium meliloti*; AAK25702, *Caulobacter crescentus*; S76334, *Synechocystis* sp. (strain PCC 6803); AAK03012, *Pasteurella multocida*; Q9KPQ4, *Vibrio cholerae*; AAB40463, AAC45723, P46885, *Escherichia coli*; P57531, *Buchnera aphidicola* (*Acyrthosiphon pisum*); NP143714, *Pyrococcus horikoshii*.

As used herein a "GNA33 polypeptide" also includes a molecule derived from a native GNA33 sequence, as well as recombinantly produced or chemically synthesized GNA33 polypeptides including the full-length GNA33 reference sequence, with or without the signal sequence (amino acids 1-21 of FIG. 3), as well as GNA33 peptides which remain immunogenic, as described below.

The term "analog" refers to derivatives of the reference molecule. The analog may retain biological activity, as described above, such as the ability to elicit formation of antibodies with functional activity against MenB. In general, the term "analog" refers to compounds having a native polypeptide sequence and structure with one or more amino acid additions, substitutions (generally conservative in nature) and/or deletions, relative to the native molecule, so long as the modifications do not destroy activity. Preferably, the analog has at least the same biological activity as the parent molecule, and may even display enhanced activity over the parent molecule. Methods for making polypeptide analogs are known in the art and are described further below.

For example, the analog will generally have at least about 50% amino acid identity to the reference molecule, more preferably about 75-85% identity and most preferably about 90-95% identity or more, to the relevant portion of the native peptide sequence in question. The amino acid sequence will have not more than about 10-75 amino acid substitutions, or not more than about 5-50 amino acid substitutions, or even only 1, 2, 3 or up to 5 substitutions, or any number between the above described ranges. Particularly preferred substitutions will generally be conservative in nature, i.e., those substitutions that take place within a family of amino acids. In this regard, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the activity. Proteins having substantially the same amino acid sequence as the reference molecule, but possessing minor amino acid substitutions that do not substantially affect the immunogenicity of the protein, are therefore within the definition of a GNA33 polypeptide. One of skill in the art may readily determine regions of the molecule of interest that can be modified with a reasonable likelihood of retaining biological activity as defined herein.

A "GNA33 peptide" is a GNA33 polypeptide, as described herein, which includes less than the full-length of the reference GNA33 molecule in question and which includes at least one epitope as defined below. Thus, a composition comprising a GNA33 peptide would include a portion of the full-length molecule but not the entire GNA33 molecule in question. Non-limiting examples of GNA33 peptides include QTP, FQTPV (SEQ ID NO:2), FQTPVHS (SEQ ID NO:3), AFQTPVHS (SEQ ID NO:4), QAFQTPVHS (SEQ ID NO:5), AQAFQTPVHS (SEQ ID NO:6), AQAFQTPVH (SEQ ID NO:7), AQAFQTPV (SEQ ID NO:8), QAFQTPVHSF (SEQ ID NO:9), AFQTPVHSFQ (SEQ ID NO: 10), FQTPVHSFQA (SEQ ID NO: 11), QTPVHSFQAK (SEQ ID NO: 12), DVSAQAFQTP [(SEQ ID NO: 12)](SEQ ID NO:55), VSAQAFQTPV (SEQ ID NO: 13) and SAQAFQTPVH (SEQ ID NO: 14).

"Molecular mimetics" of MenB are molecules that functionally mimic at least one epitope expressed on a MenB bacterium. Such molecular mimetics are useful in vaccine compositions and in eliciting antibodies for diagnostic or therapeutic applications, as described further below. Molecular mimetics include, but are not limited to: small organic compounds; nucleic acids and nucleic acid derivatives; saccharides or oligosaccharides; peptide mimetics including peptides, proteins, and derivatives thereof, such as peptides containing non-peptide organic moieties, synthetic peptides which may or may not contain amino acids and/or peptide bonds, but retain the structural and functional features of a peptide ligand; pyrrolidines; peptoids and oligopeptoids which are molecules comprising N-substituted glycine, such as those described by Simon et al. (1992) *Proc. Natl. Acad. Sci. USA* 89:9367; and antibodies, including anti-idiotype antibodies. Methods for the identification and production of molecular mimetics are described more fully below.

The term "antibody" encompasses polyclonal and monoclonal antibody preparations, as well as preparations including hybrid antibodies, altered antibodies, humanized antibodies, F(ab')$_2$ fragments, F(ab) molecules, Fv fragments, single chain fragment variable displayed on phage (scFv), single domain antibodies, chimeric antibodies and functional fragments thereof which exhibit immunological binding properties of the parent antibody molecule.

As used herein, the term "monoclonal antibody" refers to an antibody composition having a homogeneous antibody population. The term is not limited by the manner in which it is made. The term encompasses whole immunoglobulin molecules, as well as Fab molecules, F(ab')$_2$ fragments, Fv fragments, single chain fragment variable displayed on phage (scFv), humanized antibodies and other molecules that exhibit immunological binding properties of the parent monoclonal antibody molecule. Methods of making polyclonal and monoclonal antibodies are known in the art and described more fully below.

By "epitope" is meant a site on an antigen to which specific B cells and T cells respond. The term is also used interchangeably with "antigenic determinant" or "antigenic determinant site." B cell epitope sites on proteins, polysaccharides, or other biopolymers may be composed of moieties from different parts of the macromolecule that have been brought together by folding. Epitopes of this kind are referred to as conformational or discontinuous epitopes, since the site is composed of segments the polymer that are discontinuous in the linear sequence but are continuous in the folded conformation(s). Epitopes that are composed of single segments of biopolymers or other molecules are termed continuous or linear epitopes. T cell epitopes are generally restricted to linear peptides. A peptide epitope can comprise 5 or more amino acids in a spatial conformation unique to the epitope. Generally, an epitope consists of at least 5-8 such amino acids and, more usually, consists of at least 8-10 such amino acids or more. Methods of determining spatial conformation of amino acids are known in the art and include, for example, x-ray crystallography and 2-dimensional nuclear magnetic resonance spectroscopy.

Epitopes can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Computer programs that formulate hydropathy scales from the amino acid sequence of the protein, utilizing the hydrophobic and hydrophilic properties of each of the 20 amino acids, as described in, e.g., Kyte et al., *J. Mol. Biol.* (1982) 157:105-132; and Hopp and Woods, *Proc. Natl. Acad. Sci. USA* (1981) 78:3824-3828, can also be used to determine antigenic portions of a given molecule. For example, the technique of Hopp and Woods assigns each amino acid a numerical hydrophilicity value and then repetitively averages these values along the peptide chain. The points of highest local average hydrophilicities are indicative of antigenic portions of the molecule.

An antibody displays "functional activity" against a MenB organism when the antibody molecule exhibits complement-mediated bactericidal activity and/or opsonic activity against MenB as determined using the assays described herein.

By "purified" and "isolated" is meant, when referring to a polypeptide or polynucleotide, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" polynucleotide which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

By a "recombinant GNA33 polypeptide" is intended a GNA33 polypeptide having biological activity, as measured using the techniques described above and which has been prepared by recombinant DNA techniques as described herein. In general, the gene coding for the desired GNA33 polypeptide is cloned and then expressed in transformed organisms, as described further below. The host organism expresses the foreign gene to produce the GNA33 polypeptide under expression conditions. If prepared recombinantly, the polypeptides of the invention can be produced in the absence of other molecules normally present in cells. For example, GNA33 polypeptide compositions free of any trace of MenB protein contaminants can be readily obtained because the only MenB protein produced by a recombinant non-MenB host cell is the recombinant GNA33 polypeptide.

The term "polynucleotide" or "nucleic acid molecule" as used herein refers to a polymeric form of nucleotides of any length, either ribonucleotides or deoxyribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelates (e.g., metals, radioactive metals, boron, oxidative metals, etc.), those containing alkylators, those with modified linkages (e.g., alpha anomeric nucleic acids, etc.), as well as unmodified forms of the polynucleotide.

The terms "recombinant DNA molecule," or "recombinant polynucleotide" are used herein to refer to a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature. Thus, the term encompasses "synthetically derived" nucleic acid molecules.

A "coding sequence" is a nucleic acid molecule which is translated into a polypeptide, usually via mRNA, when placed under the control of appropriate regulatory sequences. The boundaries of the coding sequence may be determined by a translation start codon at the 5'-terminus and a translation stop codon at the 3'-terminus. A coding sequence can include, but is not limited to, cDNA, and recombinant nucleotide sequences.

"Control sequences" refer to nucleic acid sequences which are necessary to effect the expression of coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequences. The term "control sequences" is intended to include, at a minimum, all components necessary for expression of a coding sequence, and may also include additional components, for example, leader sequences and fusion partner sequences.

A control element, such as a promoter, "directs the transcription" of a coding sequence in a cell when RNA polymerase will bind the promoter and transcribe the coding sequence into mRNA, which is then translated into the polypeptide encoded by the coding sequence.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, blue-green algae, plant cells, yeast cells, insect cells and animal cells. Under the invention, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

By "vector" is meant any genetic element, such as a plasmid, phage, transposon, cosmid, chromosome, virus etc., which is capable of replication when associated with the proper control elements and which can transfer gene sequences between cells. Thus, the term includes cloning and expression vehicles, as well as viral vectors.

A cell has been "transformed" by an exogenous polynucleotide when the polynucleotide has been introduced inside the cell membrane. The exogenous polynucleotide may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

A "host cell" is a cell which has been transformed, or is capable of transformation, by an exogenous nucleic acid molecule.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity, or any percent identity between the specified ranges, over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Alignment may be with a sequence that has the identical number of amino acids as the sequence of interest.

Preferably, naturally or non-naturally occurring protein variants have amino acid sequences which are at least 70%, 80%, 85%, 90%, 92% or 95% or more identical to the particular GNA33 polypeptide derived from FIG. 3 (SEQ ID NO:1). More preferably, the molecules are 98% or 99% identical. Percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman, *Adv. Appl. Math.* 2:482-489 (1981).

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

The terms "effective amount" or "pharmaceutically effective amount" refer to a nontoxic but sufficient amount of the agent to provide the desired biological result. That result can be the production of antibodies with functional activity against MenB, as determined using the assays herein. Moreover, the amount may be sufficient to cause the reduction and/or alleviation of the signs, symptoms, or causes of menigococcal disease. An appropriate "effective" amount in any individual case may be determined by one of ordinary skill in the art using routine experimentation.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, the term "mammal" includes, but is not limited to, any member of the Mammalia class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender.

As used herein, the terms "immunological binding," and "immunological binding properties" refer to non-covalent interactions of the type which occur between an immunoglobulin molecule and an antigen for which the immunoglobulin is specific.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, cbromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH and β-galactosidase.

II. Modes of Carrying Out the Invention

The present invention is based on the discovery that GNA33, a lipoprotein with homology to *E. coli* murein transglycosylase, elicits protective antibodies as a result of mimicking an epitope on loop 4 of PorA in strains with serosubtype P1.2. GNA33 is not surface-exposed on live bacteria but is located in the peliplasmic space. Epitope mapping of a bactericidal anti-GNA33 mAb using overlapping peptides shows that the mAb recognizes peptides from GNA33 and PorA that share a QTP sequence that is necessary for binding. By flow cytometry, the anti-GNA33 mAb binds as well as a control anti-PorA (P1.2) mAb to the bacterial surface of most MenB strains with the P1.2 serosubtype. Anti-GNA33 antibody confers passive protection in infant rats challenged with P1.2 strains. Thus, GNA33 is a novel mimetic that elicits protective antibody directed at PorA. Unlike PorA, GNA33 elicits protective antibodies when administered without the need for renaturation of the protein. The inventors herein have discovered that GNA33 is one of the most potent mimetic antigens identified to date.

The discovery that GNA33 exhibits immunologic mimicry of the PorA P1.2 epitope evidences the utility of GNA33 for use in a vaccine for the prevention of disease caused by P1.2 strains, which represent approximately 8% of serogroup B isolates in the US (Tondella et al., *J. Clin. Microbiol.* (2000) 38:3323-3328). Further, by substituting other PorA loops into GNA33 or into subdomains of GNA33, it is possible to generate immunogenic mimetics of other serosubtype PorA epitopes useful as antigens in a multivalent meningococcal vaccine. Such a vaccine has many advantages over vaccines based on recombinant PorA. For example, the preparation of such a vaccine is greatly simplified as rGNA33 can be conveniently expressed in large amounts in non-infectious *E.* coli, without the need for detergent extractions, refolding, or for reconsitution in lipid vesicles. Also, the epitope-containing segments of PorA variants from newly emergent NmB strains causing disease can be substituted into GNA33 as needed.

Thus, GNA33 polypeptides, peptides, antibodies and other MenB mimetics can be used as diagnostic reagents and/or in compositions to prevent MenB disease. Antibodies prepared against GNA33 exhibit functional activity against MenB bacteria, wherein the functional activity is important in conferring protection against MenB disease. The antibodies can be fully characterized with respect to isotype, antigenic specificity and functional activity.

GNA33 polypeptides for use with the present invention can be isolated directly from bacteria that produce the same, using techniques known in the art. Alternatively, the polypeptides can be synthesized chemically, by any of several techniques that are known to those skilled in the peptide art. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis. The polypeptides of the present invention can also be chemically prepared by the method of simultaneous multiple peptide synthesis. See, e.g., Houghten *Proc. Natl. Acad. Sci. USA* (1985) 82:5131-5135; U.S. Pat. No. 4,631,211.

Preferably, polypeptides are produced recombinantly, by expression of a polynucleotide encoding the same, using standard techniques of molecular biology. For example, polynucleotide sequences coding for the above-described molecules can be obtained using recombinant methods, such as by screening cDNA and genomic libraries from bacteria expressing the gene, or by deriving the gene from a vector known to include the same. Furthermore, the desired gene can be isolated directly from cells containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The molecules can be designed with appropriate codons for the particular sequence. The complete sequence is then assembled from overlapping oligonucleotides prepared by standard methods and assembled into a complete coding sequence. See, e.g., Edge (1981) *Nature* 292:756; Nambair et al. (1984) *Science* 223:1299; and Jay et al. (1984) *J. Biol. Chem.* 259:6311.

Thus, particular nucleotide sequences can be obtained from vectors harboring the desired sequences or synthesized completely or in part using various oligonucleotide synthesis techniques known in the art, such polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al. (1991) *Proc. Natl. Acad. Sci. USA* 88:4084-4088. Additionally, oligonucleotide directed synthesis (Jones et al. (1986) *Nature* 54:75-82), oligonucleotide directed mutagenesis of pre-existing nucleotide regions (Riechmann et al. (1988) *Nature* 332:323-327 and Verhoeyen et al. (1988) *Science* 239:1534-1536), and enzymatic filling-in of gapped oligonucleotides using $T_4$ DNA polymerase (Queen et al. (1989) *Proc. Natl. Acad. Sci. USA* 86:10029-10033) can be used under the invention to provide molecules having altered or enhanced antigen-binding capabilities.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a sequence coding for a signal peptide or leader sequence which can later be removed by the host in post-translational processing. See, e.g., U.S. Pat. Nos. 4,431,739; 4,425,437; 4,338,397. If a signal sequence is present, it can either be the native sequence or it may be a heterologous signal sequence.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

As explained above, it may also be desirable to produce mutants or analogs of the reference GNA33 polypeptide. Mutants or analogs may be prepared by the deletion of a portion of the sequence encoding the GNA33 polypeptide, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA (*1985) 82:448; Geisselsoder et al. (1987) *BioTechniques* 5:786; Zoller and Smith (1983) *Methods Enzymol.* 100:468; Dalbadie-McFarland et al. (1982) *Proc. Natl. Acad. Sci USA* 79:6409.

The molecules can be expressed in a wide variety of systems, including insect, mammalian, bacterial, viral and yeast expression systems, all well known in the art. For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells, human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondil, Pichia pastoris, Schizosaccharomyces pombe* and *Yarrowia lipolytica.* Insect cells for use with baculovirus expression vectors include, inter alia, *Aedes aegypti, Autographa californica, Bombyx mori, Drosophila melanogaster, Spodoptera frugiperda*, and *Trichoplusia ni*.

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

Once produced, the GNA33 polypeptides can be used to produce antibodies. Thus, the polypeptides are provided in compositions to immunize mammalian subjects, including standard laboratory animals such as rodents and rabbits. The compositions may include a suitable adjuvant to elicit the production of polyclonal sera. Groups of animals are generally immunized and boosted several times with the compositions. Antisera from immunized animals can be obtained. GNA33 polypeptides that are capable of eliciting the formation of bactericidal antisera are suitable for use in the production of monoclonal antibodies. These antibodies, in turn, may be used to search for further mimetics of MenB antigens that will provide epitopes for anti-MenB vaccines.

Thus, in the practice of the invention, selected GNA33 polypeptides are used to provide monoclonal antibodies and functional equivalents thereof. The term "functional equivalent" with respect to a particular monoclonal antibody, as used herein, means a molecule that: (a) cross-blocks an exemplified monoclonal antibody; (b) binds selectively to the GNA33 polypeptide in question; (c) and, optionally, displays functional activity (e.g., complement-mediated bactericidal and/or opsonic activity) against MenB bacterial cells as determined by standard assays described below. Further, as used herein with regard to a particular monoclonal antibody-producing hybridoma of the invention, the term "progeny" is intended to include all derivatives, issue, and offspring of the parent hybridoma that produce the monoclonal antibody produced by the parent, regardless of generation or karyotypic identity.

Monoclonal antibodies are prepared using standard techniques, well known in the art, such as by the method of Kohler and Milstein, *Nature* (1975) 256:495, or a modification thereof, such as described by Buck et al. (1982) *In Vitro* 18:377. Typically, a mouse or rat is immunized with the GNA33 polypeptide conjugated to a protein carrier, boosted and the spleen (and optionally several large lymph nodes) removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and will not be rinsed away with the rest of the suspension. Resulting B-cells, or all dissociated spleen cells, are then induced to fuse with myeloma cells to form hybridomas. Representative murine myeloma lines for use in the hybridizations include those available from the American Type Culture Collection (ATCC).

More particularly, somatic cell hybrids can be prepared by the method of Buck et al., (supra), using the azaguanine resistant, non-secreting murine myeloma cell line P3X63-Ag8.653 (obtainable from the ATCC). The hybridoma cell lines are generally cloned by limiting dilution, and assayed for the production of antibodies which bind specifically to the immunizing antigen and which do not bind to unrelated antigens. The selected monoclonal antibody-secreting hybridomas are then cultured either in vitro (e.g., in tissue culture bottles or hollow fiber reactors), or in vivo (e.g., as ascites in mice).

Hybridoma supernatant can be assayed for anti-MenB-reactive antibody using, for example, either solid phase ELISA with the immunizing GNA33 polypeptide or an indirect immunofluorescence assay using MenB bacteria as the target antigen. The selectivity of monoclonal antibodies secreted by the hybridomas can be assessed using competitive specific binding assays, such as inhibition ELISA, or the like. For example, antibody molecules, either diluted in buffer, or buffer containing soluble GNA33 polypeptide, are reacted in an ELISA vessel in the presence of bound GNA33 polypeptide. After washing, bound antibody is detected by labeled anti-Ig (anti-IgM, IgG and IgA) as the secondary antibody. Antibodies that are inhibited by the soluble GNA33 polypeptide can be considered specific and, thus are selected for further study including, isotyping and additional screening for MenB binding and functional activity.

Specifically, partially purified monoclonal antibody molecules can be individually evaluated for their ability to bind to the surface of MenB using standard assays, such as those described in the examples herein. Functional activity can be determined by assessing complement-mediated bactericidal activity and/or opsonic activity. In particular, complement-mediated bactericidal activity of the antibodies can be evaluated using standard assays such as those described by Gold et al. (1970) *Infect. Immun.* 1:479, Westerink et al. (1988) *Infect. Immun.* 56:1120, Mandrell et al. (1995) *J. Infect. Dis.* 172:1279, and Granoff et al. (1995) *Clin. Diagn. Laboratory Immunol.* 2:574. In these assays, *N. meningitidis* is reacted with a complement source as well as with the antibody to be tested. Bacterial counts are done at various sampling times. Those antibodies that demonstrate complement-mediated bactericidal activity, as demonstrated by a minimum of a 50% reduction in viable bacterial cell counts determined after sixty minutes incubation with antibody and complement, as compared to colony counts at time zero, are considered to exhibit bactericidal activity for purposes of the present invention and are suitable for further use.

Complement-mediated bacteriolysis is thought to be the major mechanism responsible for host protection against invasive Meningococcal disease. However, evidence also supports an important protective role for opsonization (see, e.g., Bjerknes et al. (1995) *Infect. Immun.* 63:160). Accordingly, the opsonic activity of the antibodies produced herein can be evaluated as a second measure, or as an alternative measure, to assess functional activity. Results from opsonic assays can be used to supplement bactericidal data, and to help in the selection of antibodies capable of conferring protection. Evaluation of opsonic activity is also particularly useful herein for the evaluation of the murine monoclonal antibodies of the invention which have an IgG1 isotype. Murine IgG1 (in contrast to human IgG1) is ineffective in activation of complement. Thus, murine IgG1 antibodies do not activate complement-mediated bacteriolysis of MenB in the above-described assays. However, functional activity of IgG1 anti-GNA33 monoclonal antibodies can be assessed by opsonization in the absence of complement.

A variety of opsonic assay methods are known in the art, and can be used to evaluate functional activity of the monoclonal antibodies of the present invention. Such standard assays include those described by Sjursen et al. (1987) *Acta Path. Microbiol. Immunol. Scand., Sec. C* 95:283, Halstensen et al. (1989) *Scand. J. Infect. Dis.* 21:267, Lehmann et al. (1991) *APMIS* 99:769, Halstensen et al. (1991) *NIPH Annals* 14:157, Fredlund et al. (1992) *APMIS* 100:449, Guttormsen et al. (1992) *Infect. Immun.* 60:2777, Guttormsen et al. (1993) *J. Infec. Dis.* 167:1314, Bjerknes et al. (1995) *Infect. Immun.* 63:160, Hayrinen et al. (1995) *J. Infect. Dis.* 171:1481, de Velasco et al. (1995) *J. Infect. Dis.* 172:262, and Verheul, A. F. M. (1991) "*Meningococcal LPS Derived Oligosaccharide-Protein Conjugate Vaccines, Immunochemical and Immunological Aspects,*" Thesis, Utrecht University, The Netherlands, pp. 112-135.

Selected monoclonal antibodies of interest can be expanded in vitro, using routine tissue culture methods, or in vivo, using mammalian subjects. For example, pristane-primed mice can be inoculated with log phase hybridoma cells in PBS for ascites production. Ascites fluid can be stored at −70° C. prior to further purification.

It may be desirable to provide chimeric antibodies, especially if the antibodies are to be used in preventive or therapeutic pharmaceutical preparations, such as for providing passive protection against MenB, as well as in MenB diagnostic preparations. Chimeric antibodies composed of human and non-human amino acid sequences may be formed from the mouse monoclonal antibody molecules to reduce their immunogenicity in humans (Winter et al. (1991) *Nature* 349:293; Lobuglio et al. (1989) *Proc. Nat. Acad. Sci. USA* 86:4220; Shaw et al. (1987) *J Immunol.* 138:4534; and Brown et al. (1987) *Cancer Res.* 47:3577; Riechmann et al. (1988) *Nature* 332:323; Verhoeyen et al. (1988) *Science* 239:1534; and Jones et al. (1986) *Nature* 321:522; EP Publication No. 519,596, published 23 Dec. 1992; and U.K. Patent Publication No. GB 2,276,169, published 21 Sep. 1994).

Antibody molecule fragments, e.g., $F(ab')_2$, Fv, and sFv molecules, that are capable of exhibiting immunological binding properties of the parent monoclonal antibody molecule can be produced using known techniques. Inbar et al. (1972) *Proc. Nat. Acad. Sci. USA* 69:2659; Hochman et al. (1976) *Biochem* 15:2706; Ehrlich et al. (1980) *Biochem* 19:4091; Huston et al. (1988) *Proc. Nat. Acad. Sci. USA* 85(16):5879; and U.S. Pat. Nos. 5,091,513 and 5,132,405, to Huston et al.; and U.S. Pat. No. 4,946,778, to Ladner et al.

In the alternative, a phage-display system can be used to expand the monoclonal antibody molecule populations in vitro. Saiki, et al. (1986) *Nature* 324:163; Scharf et al. (1986) *Science* 233:1076; U.S. Pat. Nos. 4,683,195 and 4,683,202; Yang et al. (1995) *J Mol Biol* 254:392; Barbas, III et al. (1995) *Methods. Comp. Meth Enzymol* 8:94; Barbas, III et al. (1991) *Proc Natl Acad Sci USA* 88:7978.

Once generated, the phage display library can be used to improve the immunological binding affinity of the Fab molecules using known techniques. See, e.g., Figini et al. (1994) *J. Mol. Biol.* 239:68.

The coding sequences for the heavy and light chain portions of the Fab molecules selected from the phage display library can be isolated or synthesized, and cloned into any suitable vector or replicon for expression. Any suitable expression system can be used, including, for example, bacterial, yeast, insect, amphibian and mammalian systems. Expression systems in bacteria include those described in Chang et al. (1978) *Nature* 275:615, Goeddel et al. (1979) *Nature* 281:544, Goeddel et al. (1980) *Nucleic Acids Res.* 8:4057, European Application No. EP 36,776, U.S. Pat. No. 4,551,433, deBoer et al. (1983) *Proc. Natl. Acad. Sci. USA* 80:21-25, and Siebenlist et al. (1980) *Cell* 20:269.

Expression systems in yeast include those described in Hinnen et al. (1978) *Proc. Natl. Acad. Sci. USA* 75:1929, Ito et al. (1983) *J. Bacteriol.* 153:163, Kurtz et al. (1986) *Mol. Cell. Biol.* 6:142, Kunze et al. (1985) *J. Basic Microbiol.* 25:141, Gleeson et al. (1986) *J. Gen. Microbiol.* 132:3459, Roggenkamp et al. (1986) *Mol. Gen. Genet.* 202:302, Das et al. (1984) *J. Bacteriol.* 158:1165, De Louvencourt et al. (1983) *J. Bacteriol.* 154:737, Van den Berg et al. (1990) *Bio/Technology* 8:135, Kunze et al. (1985) *J. Basic Microbiol.* 25:141, Cregg et al. (1985) *Mol. Cell. Biol.* 5:3376, U.S. Pat. Nos. 4,837,148 and 4,929,555, Beach et al. (1981) *Nature* 300:706, Davidow et al. (1985) *Curr. Genet.* 10:380, Gaillardin et al. (1985) *Curr. Genet.* 10:49, Ballance et al. (1983) *Biochem. Biophys. Res. Commun.* 112:284-289, Tilburn et al. (1983) *Gene* 26:205-221, Yelton et al. (1984) *Proc. Natl. Acad. Sci. USA* 81:1470-1474, Kelly et al. (1985) *EMBO J.* 4:475479; European Application No. EP 244,234, and International Publication No. WO 91/00357.

Expression of heterologous genes in insects can be accomplished as described in U.S. Pat. No. 4,745,051, European Application Nos. EP 127,839 and EP 155,476, Vlak et al. (1988) *J Gen. Virol.* 69:765-776, Miller et al. (1988) *Ann. Rev.*

Microbiol. 42:177, Carbonell et al. (1988) *Gene* 73:409, Maeda et al. (1985) *Nature* 315:592-594, Lebacq-Verheyden et al. (1988) *Mol. Cell. Biol.* 8:3129, Smith et al. (1985) *Proc. Natl. Acad. Sci. USA* 82:8404, Miyajima et al. (1987) *Gene* 58:273, and Martin et al. (1988) *DNA* 7:99. Numerous baculoviral strains and variants and corresponding permissive insect host cells from hosts are described in Luckow et al. (1988) *Bio/Technology* 6:47-55, Miller et al. (1986) GENERIC ENGINEERING, Setlow, J. K. et al. eds., Vol. 8, Plenum Publishing, pp. 277-279, and Maeda et al. (1985) *Nature* 315:592-594.

Mammalian expression can be accomplished as described in Dijkema et al. (1985) *EMBO J.* 4:761, Gorman et al. (1982) *Proc. Natl. Acad. Sci. USA* 79:6777, Boshart et al. (1985) *Cell* 41:521, and U.S. Pat. No. 4,399,216. Other features of mammalian expression can be facilitated as described in Ham et al. (1979) *Meth. Enz.* 58:44, Barnes et al. (1980) *Anal. Biochem.* 102:255, U.S. Pat. Nos. 4,767,704, 4,657,866, 4,927,762, 4,560,655 and Reissued U.S. Pat. No. RE 30,985, and in International Publication Nos. WO 90/103430, WO 87/00195.

Any of the above-described antibody molecules can be used herein to provide anti-MenB therapeutic or preventive pharmaceutical agents. Additionally, "humanized" antibody molecules, comprising antigen-binding sites derived from the instant murine monoclonal antibodies, can be produced using the techniques described above.

The anti-MenB antibodies of the present invention, described above, are conveniently used as receptors to screen diverse molecular libraries in order to identify molecular mimetics of epitopes from MenB, using methods such as those described in U.S. Pat. Nos. 6,030,619 and 6,048,527, incorporated by reference herein in their entireties. Methods for identifying mimetics in molecular libraries generally involve the use of one or more of the following procedures: (1) affinity purification with an immobilized target receptor; (2) binding of a soluble receptor to tethered ligands; and (3) testing soluble compounds directly in antigen competition assays or for biological activity. Molecules screened for molecular mimics include but are not limited to small organic compounds, combinatorial libraries of organic compounds, nucleic acids, nucleic acid derivatives, saccharides or oligosaccharides, peptoids, soluble peptides, peptides tethered on a solid phase, peptides displayed on bacterial phage surface proteins, bacterial surface proteins or antibodies, and/or peptides containing non-peptide organic moieties.

For example, libraries of diverse molecular species can be made using combinatorial organic synthesis. See, e.g., Gordon et al. (1994) *J. Med. Chem.* 37:1335. Examples include but are not limited to pyrrolidines; oligocarbamates (Cho et al. (1993) *Science* 261:1303); peptoids such as N-substituted glycine polymers (Simon et al. (1992) *Proc. Natl. Acad. Sci. USA* 89:9367); and vinylogous polypeptides (Hagihara et al. (1992) *J. Am. Chem. Soc.* 114:6568).

A variety of approaches, known in the art, can be used to track the building blocks as they are added during synthesis so that the history of individual library members can be determined. These approaches include addressable location on a photolithographic chip (oligocarbamates), a deconvolution strategy in which "hits" are identified through recursive additions of monomers to partially synthesized libraries (peptoids, pyrrolidines, peptides), and coding combinatorial libraries by the separate synthesis of nucleotides (Nielsen et al. (1993) *J. Am. Chem. Soc.* 115: 9812) or other organic moieties (Ohlmeyer et al. (1993) *Proc. Natl. Acad. Sci. USA* 90:10922) ("tags"). The coded tags associated with each library member can then be decoded after a mimetic has been selected. For example, nucleic acid tags can be decoded by DNA sequencing.

Peptoid combinatorial libraries are particularly useful for identifying molecular mimetics of MenB epitopes. Peptoids are oligomers of N-substituted glycine (Simon et al. (1992) *Proc. Natl. Acad. Sci. USA* 89:9367) and can be used to generate chemically diverse libraries of novel molecules. The monomers may incorporate t-butyl-based side-chain and 9-fluorenyl-methoxy-carbonyl a-amine protection. The assembly of monomers into peptoid oligomers can be performed, for example, on a solid phase using the "submonomer method" of Zuckermann et al. (1992) *J. Am. Chem. Soc.* 114:10646. In this method, syntheses are conducted with Rink amide polystyrene resin (Rink et al. (1987) *Tetrahedron Lett.* 28:3787). Resin-bound amines are bromoacetylated by in situ activation of bromoacetic acid with diisopropyl-carbodiimide. Subsequently, the resin-bound bromoacetamides are displaced by addition of an amine. The amines may incorporate t-butyl-based protection of additional reactive groups. This two-step cycle is repeated until the desired number of monomers is added. The oligopeptide is then released from the resin by treatment with 95% trifluroacetic acid/5% water. The syntheses are performed, preferably, using a robotic synthesizer. See, e.g., Zuckermann et al. (1992) *Pept. Protein Res.* 40:498; and Zuckermann et al. (1996) *Methods in Enzymology* 267:437. In the alternative, oligomerization of the peptoid monomers may be performed by in situ activation by either benzotriazol-1-yloxytris (pyrrolidino)phosphonium hexafluorphosphate or bromotris(pyrrolidino) phosphonium hexafluorophosphate. In this alternative method, the other steps are identical to conventional peptide synthesis using a-(9-fluorenyl methoxycarbonyl) amino acids (see, e.g., Simon et al. (1992), supra).

Once the peptoid libraries are generated, they can be screened by, e.g., adding the monoclonal antibodies of the present invention, along with various pools of the combinatorial peptoids, to wells of microtiter plates coated with MenB polypeptides or MenB bacteria. After a period of incubation and a wash to remove unbound antibody, the presence of bound antibody is determined by standard ELISA assays. See, e.g., Harlow & Lane, *Antibodies: A Laboratory Manual* (1988), Cold Spring Harbor Laboratory, Cold Spring Harbor, N.Y., 553. Wells that do not contain bound antibody indicate the presence of peptoid mimetics that bind to the antibody. The particular identities of the peptoid mimetics in the pools are determined by recursively adding back monomer units to partially synthesized members of the libraries. Zuckermann et al. (1994) *J. Med. Chem.* 37:2678. Other methods for identifying active compounds in pools of small molecules include fractionating the pool by reverse phase HPLC or affinity selection/mass spectroscopy (Nedved M. L. Et al (1996) *Anal. Chem.* 68:4228).

Once putative molecular mimetics are identified, they are tested for their ability to elicit functionally active (e.g., bactericidal and/or opsonic) antibodies, as described above. Molecular mimetics that have these properties are appropriate for further use, for example, in vaccine compositions.

The GNA33 antibodies, as well as molecular mimetics identified using the functionally active anti-MenB antibodies of the invention can be used to generate antibody reagents for use in diagnostic assays. For example, the GNA33 antibodies described herein, as well as further antibodies reactive with the molecular mimetics, can be used to detect bacterial antigen in biological samples using immunodiagnostic techniques such as competition, direct reaction, or sandwich type assays. Such assays include Western blots; agglutination tests; enzyme-labeled and mediated immunoassays, such as ELISAs; biotin/avidin type assays; radioimmunoassays; immunoelectrophoresis; immunoprecipitation, and the like. The reactions generally include revealing labels such as fluorescent, chemiluminescent, radioactive, enzymatic labels or dye molecules, or other methods for detecting the formation of a complex between the mimetic and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more MenB antigens or molecular mimetics) under suitable binding conditions such that the component is sufficiently immobilized to the support. Sometimes, immobilization to the support can be enhanced by first coupling to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigen or mimetic to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. *Bioconjugate Chem.* (1992) 3:2-13; Hashida et al., *J. Appl. Biochem.* (1984) 6:56-63; and Anjaneyulu and Staros, *International J. of Peptide and Protein Res.* (1987) 30:117-124.

After reacting the solid support with the solid phase component, any non-immobilized solid-phase components are removed from the support by washing, and the support-bound component is then contacted with a biological sample suspected of containing ligand moieties (e.g., MenB antibodies) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with a MenB epitope or mimetic according to the present invention. A biological sample containing or suspected of containing anti-MenB immunoglobulin molecules is then added to the coated wells. After a period of incubation sufficient to allow antibody binding to the immobilized molecule, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound MenB ligands from a biological sample can be readily detected using a secondary binder comprising an antibody directed against the antibody ligands. A number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the MenB epitopes or mimetics and antibodies specific for these molecules form complexes under precipitating conditions. In one particular embodiment, the molecules can be attached to a solid phase particle (e.g., an agarose bead or the like) using coupling techniques known in the art, such as by direct chemical or indirect coupling. The coated particle is then contacted under suitable binding conditions with a biological sample suspected of containing antibodies for MenB. Cross-linking between bound antibodies causes the formation of particle-epitope or mimetic-antibody complex aggregates which can be precipitated and separated from the sample using washing and/or centrifugation. The reaction mixture can be analyzed to determine the presence or absence of complexes using any of a number of standard methods, such as those immunodiagnostic methods described above.

In yet a further embodiment, an immunoaffinity matrix can be provided, wherein a polyclonal population of antibodies from a biological sample suspected of containing MenB antibodies is immobilized to a substrate. In this regard, an initial affinity purification of the sample can be carried out using immobilized antigens. The resultant sample preparation will thus only contain anti-MenB moieties, avoiding potential nonspecific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, labeled molecules are contacted with the bound antibodies under suitable binding conditions. After any non-specifically bound MenB epitope or mimetic has been washed from the immunoaffinity support, the presence of bound antigen can be determined by assaying for label using methods known in the art.

The above-described assay reagents, including the GNA33 polypeptides and/or mimetics of the invention or antibodies thereto, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

In addition, the GNA33 polypeptides, molecular mimetics and antibodies, can be used herein to prevent MenB disease in mammalian subjects. Particularly, vaccine compositions containing these molecules can be used for the prevention of MenB disease in vaccinated subjects. The vaccines may be administered in conjunction with other antigens and immunoregulatory agents, for example, immunoglobulins, cytokines, lymphokines, and chemokines, including but not limited to IL-2, modified IL-2 (cys125 to ser125), GM-CSF, IL-12, g-interferon, IP-10, MIP1b and RANTES.

The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

Adjuvants may also be used to enhance the effectiveness of the vaccines. Adjuvants can be added directly to the vaccine compositions or can be administered separately, either concurrently with or shortly after, vaccine administration. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837; Chapter 10 in Vaccine design: the subunit and adjuvant approach, eds. Powell & Newman, Plenum Press 1995), containing 5% Squalene, 0.5% TWEEN®-80, and 0.5% SPAN® 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% TWEEN®-80, 5% phironic-blocked polymer L121, and thr-MDP either microfluidized into a submicron emulsion or vortexed to generate a larger particle size emulsion, and (c) RIBI™ adjuvant system (RAS), (Ribi Immunochen, Hamilton, Mont.) containing 2% Squalene, 0.2% TWEEN®-80, and one or more bacterial cell wall components from the group consisting of monophosphorylipid A (MPL), trehalose dimycolate (TDM), and cell wall skeleton (CWS), preferably MPL+CWS (DETOX™); (3) saponin adjuvants, such as QS21 or STIMULON™ (Cambridge Bioscience, Worcester, Mass.) may be used or particles generated therefrom such as ISCOMs (immunostimulating complexes), which ISCOMs may be devoid of additional detergent, see, e.g., International Publication No. WO 00/07621; (4) Complete Freund's Adjuvant (CFA) and Incomplete Freund's Adjuvant (IFA); (5) cytokines, such as interleukins (IL-1, IL-2, IL-4, IL-5, IL-6, IL-7, IL-12 (International Publication No. WO 99/44636), etc.), interferons (e.g., gamma interferon), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where seine is substituted for the wild-type amino acid at position 109), and PT-K9/G129 (where lysine is substituted for the wild-type amino acid at position 9 and glycine substituted at position 129) (see, e.g., International Publication Nos. W093/13202 and W092/19265); (7) MPL or 3-O-deacylated MPL (3dMPL) (see, e.g., GB 2220221), EP-A-0689454, optionally in the substantial absence of alum when used with pneumococcal saccharides (see, e.g., International Publication No. WO 00/56358); (8) combinations of 3dMPL with, for example, QS21 and/or oil-in-water emulsions (see, e.g., EP-A-0835318, EP-A-0735898, EP-A-0761231; (9) oligonucleotides comprising CpG motifs (see, e.g., Roman et al. (1997) Nat. Med. 3:849-854; Weiner et al. (1997) Proc. Natl. Acad. Sci. USA 94:10833-10837; Davis et al. (1998) J. Immunol. 160:870-876; Chu et al. (1997) J. Exp. Med. 186:1623-1631; Lipford et al. (1997) Eur. J. Immunol. 27:2340-2344; Moldoveanu et al. (1988) Vaccine 16:1216-1224; Krieg et al. (1995) Nature 374:546-549; Klinman et al. (1996) Proc. Natl. Acad. Sci. USA 93:2879-2883; Ballas et al. (1996) J. Immunol. 157:1840-1845; Cowdery et al. (1996) J. Immunol. 156: 4570-4575; Halpern et al. (1996) Cell Immunol. 167:72-78; Yamamoto et al. (1988) Jpn. J. Cancer Res. 79:866-873; Stacey et al. (1996) J. Immunol. 157:2116-2122; Messina et al. (1991) J. Immunol. 147:1759-1764; Yi et al. (1996) J. Immunol. 157:4918-4925; Yi et al. (1996) J. Immunol. 157: 5394-5402; Yi et al. (1998) J. Immunol. 160:4755-4761; Yi et al. (1998) J. Immunol. 160:5898-5906; International Publication Nos. WO 96/02555, WO 98/16247, WO 98/18810, WO 98/40100, WO 98/55495, WO 98/37919 and WO 98/52581), such as those containing at least on CG dinucleotide, with cytosine optionally replaced with 5-methylcytosine; (10) a polyoxyethylene ether or a polyoxyethylene ester (see, e.g., International Publication No. WO 99/52549); (11) a polyoxyethylene sorbitan ester surfactant in combination with an octoxynol (see, e.g., International Publication No. WO 01/21207) or a polyoxyethylene alkyl ether or ester surfactant in combination with at least one additional non-ionic surfactant such as an octoxynol (see, e.g., International Publication No. WO 01/21152); (12) a saponin and an irnmunostimulatoiy oligonucleotide such as a CpG oligonucleotide (see, e.g., International Publication No. WO 00/62800); (13) an immunostimulant and a particle of metal salt (see, e.g., International Publication No. WO 00/23105); and (14) other substances that act as immunostimulating agents to enhance the effectiveness of the composition.

Muramyl peptides include, but are not limited to, N-acetyl-muramyl-L-threonyl-D-isoglutamine (thr-MDP), -acetyl-normuramyl-L-alanyl-D-isogluatme (nor-MDP), -acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

In order to enhance the effectiveness of the compositions, it may be necessary to conjugate the active agent to a carrier molecule. Such carrier molecules will not themselves induce the production of harmful antibodies. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), inactive virus particles, $CRM_{197}$ (a nontoxic mutant diphtheria toxin), and the like. Such carriers are well known to those of ordinary skill in the art.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes, or adsorbed to particles for enhanced adjuvant effect, as discussed above.

The vaccines will comprise an effective amount of the active agent, such as GNA33 polypeptide or antibody thereto, and any other of the above-mentioned components, as needed. By "an effective amount" is meant an amount of a molecule which will induce an immunological response in the individual to which it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or gd T cell populations.

Once formulated, the vaccines are conventionally administered parenterally, e.g., by injection, either subcutaneously or intramuscularly. Additional formulations suitable for other modes of administration include oral and pulmonary formulations, suppositories, and transdermal applications. Dosage treatment may be a single dose schedule or a multiple dose schedule.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Bacterial Strains.

*N. meningitidis* serogroup B strains included in this study were isolated from patients with meningococcal disease residing in different countries, and were collected over a period of 36 years. 21 strains were serogroup B strains and one strain was a serogroup C strain. The strains are summarized in Table 1. Based on electrophoretic typing (ET), the collection represents a broad range of genetic diversity for MenB strains causing disease.

Mutants of strains MC58, BZ232 and NMB (MC58ΔGNA33, BZ232ΔGNA33, and NMBΔGNA33, respectively) in which the gna33 gene was deleted and replaced by allelic exchange with an antibiotic cassette were prepared by transforming the parent strain with the plasmid pBSUD33ERM. This plasmid contains the upstream and downstream flanking gene regions for allelic exchange and the ermC gene (erythromycin resistance). Briefly, the upstream flanking region (including the start codon) from −867 to +75 and the downstream flanking region (including the stop codon) from +1268 to +1744, were amplified from MC58 using the following primers:

```
U33FOR 5'-GCTCTAGAGATGAGTCGAACACAATGAACAATGTCCTGA-3';    (SEQ ID NO:26)

U33REV 5'-TCCCCCGGGCTCTTGCTTTGGCAGGCGGCGA-3';            (SEQ ID NO:27)

D33FOR 5'-TCCCCCGGGCACGGGATATGTGTGGC-3',                 (SEQ ID NO:28)

D33REV 5'-CCCGCTCGAGAGTAGGGACAACCGG-3'.                  (SEQ ID NO:29)
```

The fragments were cloned into pBluescript (Stratgene, Milan, Italy) and transformed into *E. coli* DH5 using standard techniques (Sambrook and Russell, *Molecular Cloning: A Laboratory Manual* (2001)). Once all subcloning was complete, naturally competent *Neisseria* strains MC58, BZ232 and NMB were transformed by selecting a few colonies grown overnight on chocolate agar plates (Remel, Laztakas, KA) and mixing them with 20 µl of 10 mM Tris-HCl pH 6.5 containing 1 µg of plasmid DNA. The mixture was spotted onto a chocolate agar plate, incubated for 6 hrs at 37° C., 5% $CO_2$ then diluted in PBS and spread on chocolate agar plates containing 7 µg/ml of erythromycin. The absence of the gna33 gene in the genome of the erythromycin-resistant colonies for each of the three strains was confirmed by PCR using the following primers:

```
F33
5'-GCTCTAGAGGGCGACGACAGGCGG-3' and     (SEQ ID NO:30)

R33
5'-CCCGCTCGAGTTACGGGCGGTATTCGG-3'.     (SEQ ID NO:31)
```

These primers correspond to the 5'-sense and 3'-antisense strands, respectively, of the gna33 gene. Lack of GNA33 expression was confirmed by western blot analysis as described below.

Monoclonal Antibody (mAb) Reagents.

Antibodies used for flow cytometry, bactericidal, and in vivo protection experiments included the following: a meningococcal Por A P1.2-specific subtyping mAb (MN16C13F4, subclass IgG2a) obtained from Rijksinstituut Voor Volksgezondheid en Mileu, Bilthoven, The Netherlands, or from Wendell Zollinger, Walter Reed Army Institute of Research, Washington D.C.); anti-polysaccharide mAbs specific for encapsulated serogroup B, SEAM 12 and SEAM 3 (Granoff et al., *J. Immunol.* (1998) 160:5028-5036), subclass IgG2a), and serogroup C (mAb 181.1 (Garcia-Ojeda et al., *Infect. Immun.* (2000) 68:239-246, subclass IgG3). MAb 181.1 was provided by Kathryn Stein, U.S. Food and Drug Administration. The negative control consisted of a mouse IgG mAb (VIG10) of irrelevant specificity, or mouse polyclonal antiserum prepared against *E. coli* proteins from the strain used to express rGNA33.

Expression and Purification of GNA33.

The gna33 ORF was amplified by PCR on chromosomal DNA from strain 2996 (P. van der Ley and J. T. Poolman, *Infect. Immun.* (1992) 60:3156, 1992) with synthetic oligonucleotides used as primers. The amplified DNA fragment was cloned into pET-21b+ vector (Novagen, Madison, Wis.) to express the protein as His-tagged (HT-GNA33) or as a soluble protein without the signal and lipid modification sequences (rGNA33). The expression of recombinant protein was evaluated by SDS-polyacrylamide gel electrophoresis, performed as described. The His-tagged protein was purified by affinity chromatography on $Ni^{2+-}$ conjugated chelating fast flow Sepharose (Amersham-Pharmacia Biotech, Uppsala, Sweden) and the untagged form was purified by FPLC using a mono S ion-exchange resin (Amersham-Pharmacia).

Preparation of Polyclonal Anti-GNA33 Antisera.

In order to prepare antisera against GNA33, 20 µg of purified HT-GNA33 or untagged rGNA33 was used to immunize six-week old CD1 female mice (four to ten mice per group). The mice were obtained from Charles River (Italia S.P.A., Calco, Italy, or Hollister, Calif.). The recombinant protein was given i.p, together with complete Freund's adjuvant (CFA) for the first dose and incomplete Freund's adjuvant (IFA) for the second (day 21) and third (day 35) booster doses. Blood samples were taken on days 34 and 49.

Preparation of Monoclonal Antibodies.

Four to six weeks old female CD1 mice were immunized as described above except that the third dose was given without adjuvant. Three days later, mice were sacrificed and their spleen cells were fused with myeloma cells P3X63-Ag8.653 at a ratio of 5 spleen cells to 1 myeloma cells. After two weeks incubation in HAT selective medium, hybridoma supernatants were screened for antibody binding activity by ELISA, performed on microtiter plates coated with the noncapsulated *N. meningitidis* strain, M7 (Stephens et al., *Infect. Immun.* (1991) 59:4097-4102) that had been inactivated by treatment with 0.025% paraformaldehyde. Hybridomas secreting GNA33-specific antibody were cloned twice by limiting dilution and then expanded and frozen for subsequent use in tissue culture, or for ascites production in BALB/c mice.

The subclasses of the monoclonal antibodies were determined using a mouse monoclonal antibody isotyping kit (Amersham-Pharmacia.). Among the selected mAbs, one IgG2a anti-GNA33 mAb, designated mAb 25, was used in all of the binding and functional studies described below. This monoclonal antibody was purified from mouse ascites by Hi-Trap affinity columns (Amersham-Pharmacia) and, after exhaustive dialysis in PBS buffer, the concentration of the purified mAb was determined using a modified Lowry method with BSA as a standard (DC, Bio-Rad, Rome, Italy). Specificity of mAb 25 binding was determined by Western blot using membrane proteins prepared from strains MC58, BZ232 and NMB, and their respective GNA33 knockouts (MC58ΔGNA33, BZ232ΔGNA33 and NMBΔGNA33; see below).

Binding of Antisera to the Surface of Live Encapsulated Meningococci.

Figure 1B:
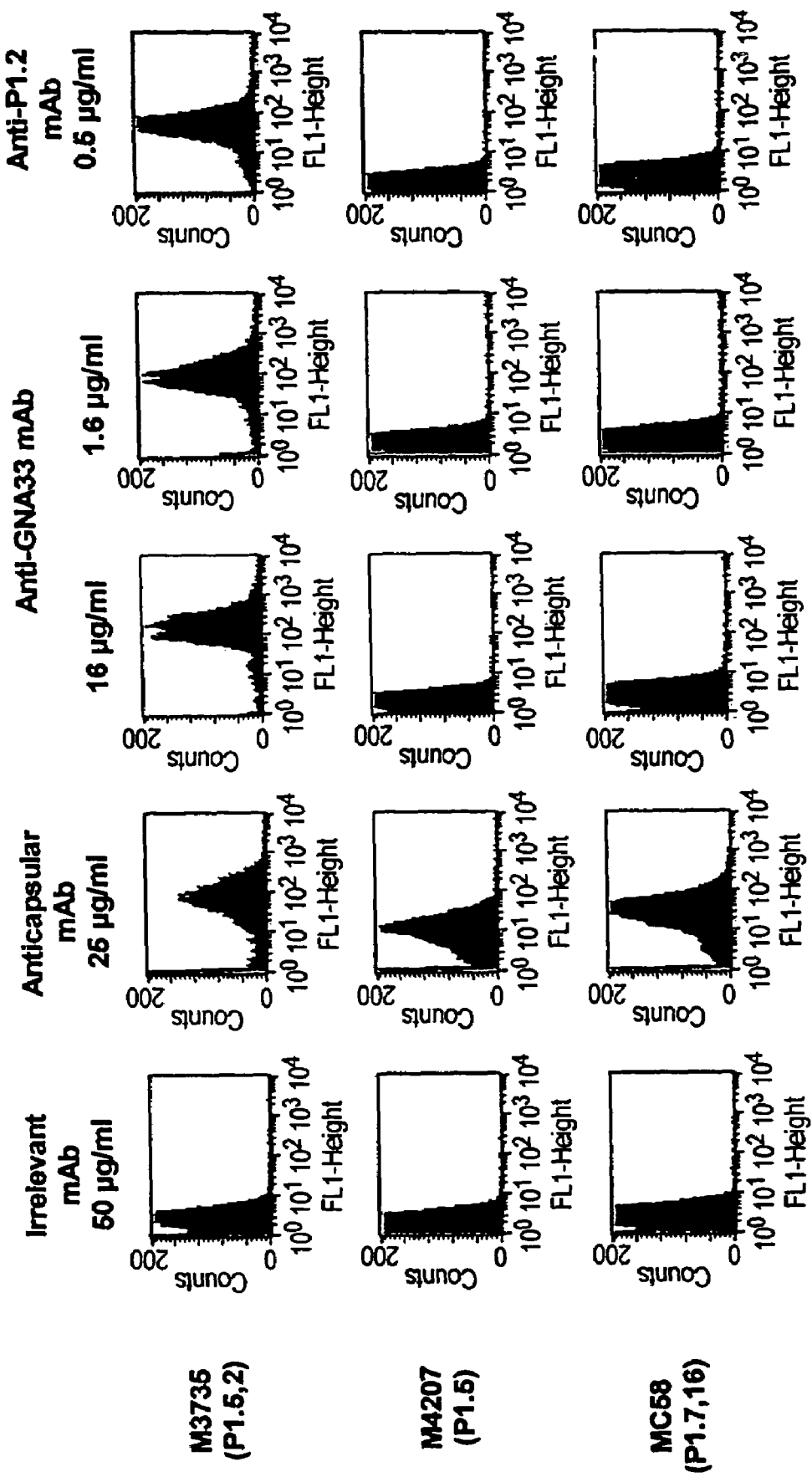

The ability of the polyclonal anti-GNA33 antisera and mAb 25 to bind to the surface of live NmB strains was determined using a flow cytometric detection of indirect fluorescence assay, performed as described previously (Moe et al., *Infect. Immun.* (1999) 67:5664-5675). FIG. 1A shows binding of polyclonal anti-rGNA33 antisera to four representative NmB strains, the parent strain, 2996 (P1.5,2), and three other strains M3735 (P1.5,2), M4207 (P1.5) and MC58 (P1.7,16). The anti-GNA33 polyclonal antiserum reacted only with strains 2996 and M3735. The anticapsular positive control mAb bound to all four strains, whereas the negative control antiserum prepared from animals immunized with *E. coli* proteins, showed only background binding. FIG. 1B shows the results of similar experiments measuring binding of the anti-GNA33 mAb 25 to the bacterial cell surface of three strains (M3735 [P1.5,2], M4207 [P1.5] and MC58 [P1.7, 16]). The mAb bound only to strain M3735 (P1.5,2).

Table I summarizes the results of flow cytometry experiments measuring the ability of anti-GNA33 antisera or mAb 25 to bind to the surface of live bacteria from 22 genetically diverse encapsulated meningococcal strains (21 serogroup B and 1 serogroup C). The anti-GNA33 antibody bound only to strains with the P1.5,2 or P1.2 serosubtypes (9 of 9 vs. 0 of 13 strains with other PorA serosubtypes; P<0.001). One of the nine positive strains, M986, showed lower binding than the other eight strains (vide infra). There was no binding to three strains (M4207, 1000, and BZ83) that express the P1.5 epitope present on loop 1 of PorA but not the P1.2 epitope (loop 4). Also, there was no binding to strain M136, which does not express PorA (i.e. P1-). These data indicate that binding of anti-GNA33 antibody to the bacterial surface correlates with expression of the PorA serosubtype P1.2.

Complement-Dependent Bactericidal Antibody Activity.

Bactericidal activity was measured a previously described (Moe et al., *Infect. Immun.* (2001) 69:3762-3771). Except where noted, the complement source was human serum from a healthy adult (MAS) with no detectable anticapsular antibody to serogroup B or C polysaccharide as tested by ELISA, and no detectable intrinsic bactericidal activity against the target strains when tested at a final serum concentration of 20 or 40%. In a few experiments described below, bactericidal activity was measured using serum from a patient with untreated agammaglobulinemia (Steele et al., *Infect. Immun.* (1984) 44:452-458), infant rabbit serum or adult rat serum as complement sources.

Animal Protection.

The ability of anti-GNA33 antibodies to confer passive protection against *N. meningitidis* serogroup B bacteremia was tested in infant rats challenged i.p. The assay was performed as previously described (Moe et al., *Infect. Immun.* (1999) 67:5664-5675). In brief, on the morning of the challenge, colonies were picked, inoculated into a broth culture, and grown and prepared as described above for the bactericidal assay. With strain M986, to maximize sensitivity, the animals were injected i.p. at time 0 with 100 μl of different dilutions of test or control antisera mixed with approximately $5 \times 10^3$ of the challenge MenB test strain. In experiments with other test strains, the antibody was administered i.p. at time 0 and the bacterial challenge was performed i.p. 2 hours later. The positive control anticapsular mAb used was SEAM 3. Blood specimens were obtained 18 h after the bacterial challenge by cardiac puncture with a needle and syringe containing approximately 10 μl heparin without preservative (1000 Units/ml; Fujisawa USA, Deerfield, Ill.). Aliquots of 1, 10 and 100 μL of blood were plated onto chocolate agar. The CFU per ml of blood was determined after overnight incubation of the plates at 37° C. in 5% $CO_2$. For calculation of geometric mean CFR/ml, animals with sterile cultures were assigned a value of 1 CFR/ml.

SDS-PAGE and Western Blots.

Total cell extracts of meningococcal strains were prepared as follows. Single colonies were grown in 7 mL of Mueller-Hinton broth (Difco, Detroit, Mich.) supplemented with 0.25% glucose to an $A_{620\ nm}$ of 0.5-0.7. The bacteria were collected by centrifugation at 5000×g for 15 mm and resuspended in PBS. After freeze-thawing, the bacterial suspension was mixed with sample buffer (0.06 M Tris-HCl, pH 6.8, 10% (v/v) glycerol, 2% (w/v) SDS, 5% (v/v) 2-mercaptoethanol) and boiled 10 min. Purified proteins (0.5 μg/lane), or total cell extracts (25 μg) derived from meningococcal strains were loaded onto a 12.5% SDS-polyacrylamide gels (Laemmli, U.K. *Nature* (1970) 227:680-685) and transferred to a nitrocellulose membrane (Towbin et al., *Proc. Natl. Acad. Sci.* (1979) 76:4350-4354). The transfer was performed for 2 hours at 150 mA at 4° C., using transfer buffer (0.3% Tris base, 1.44% glycine, 20% (v/v) methanol). The nitrocellulose membrane was saturated by overnight incubation at 40° C. in saturation buffer (10% skimmed milk, 0.1% TRITON® in PBS). The membrane was washed twice with washing buffer (3% skimmed milk, 0.1% TRITON® in PBS) and incubated for 2 hours at 37° C. with mouse antisera diluted 1:200 in washing buffer, mAb 25 at a final concentration of 6 μg/ml, or a 1:100 dilution of an anti-Por A P1.2 mAb followed by a 1:2000 dilution of horseradish peroxidase labelled anti-mouse Ig (Dako, Glostrup, Denmark). The membrane was washed twice with 0.1% TRITON® X100 in PBS and developed with the Opti-4CN Substrate Kit (Bio-Rad). The reaction was stopped by adding water.

Peptide Spot Synthesis.

Peptide spot synthesis was carried out on amino-PEG-cellulose membranes (ABIMED, Langerfeld, Germany) using a model ASP 222 automated spot synthesizer (ABIMED) and diisopropylcarbodiimide (DIC)/N-hydroxy-benzotriazole (HOBt) activation (Frank and Overwin, *Methods Mol. Biol.* (1996) 66:149-169). In situ-prepared 0.2 M HOBt esters of fluorenylmethoxycarbonyl (Fmoc)-amino acid derivatives were used for the coupling reaction. Free amino functions on the spots were treated with a solution of bromophenol blue in dimethylformammide, which resulted in a blue staining that allowed for the visual monitoring of all synthesis steps. After the final cycle, all the peptides were N-terminally acetylated with 2% acetic anhydride. At the end of the synthesis, the side-chain protecting groups were removed using a mixture of trifluoroacetic acid/triisobutylsilane/water/dichloromethane (50/3/2/45).

Peptide Binding Assay.

Cellulose-bound peptides were soaked in ethanol to prevent hydrophobic interactions between the peptides. Nonspecific binding was blocked by incubating cellulose sheets overnight at 4° C. with 10 ml of 2% casein in Tris buffered saline (TBS: 50 mM Tris-HCl, 137 mM NaCl, 27 mM KCl, pH 7.0), containing 0.05% TWEEN® 20 (T-TBS). The sheets were incubated for 2 hr at 37° C. with the anti-GNA33 mAb 25 (6 μg/ml) or an anti-PorA 1.2 mAb diluted 1:100 in T-TBS blocking buffer. Alkaline phosphatase-conjugated goat anti-mouse IgG (BioRad) was then added at 1:3000 dilution in T-TBS blocking buffer for 1 hr at 37° C. Sheets were washed three times with T-TBS and detection of binding was achieved by incubating the sheets with bromo-4-chloro-3-indolyl-phosphate (BCIP) (Sigma, Steinheim, Germany) and 3-(4,5-dimethylthiazol-2-yl)-2,5 diphenyl-tetrazolium bromide (MTT; Sigma) in substrate buffer (100 mM Tris, pH 8.9, 100 mM NaCl, 2 mM MgCl$_2$). Quantitative evaluation of the signal was obtained using a Umax Speedy II 2200 optical scanner.

EXAMPLE 1

Binding of Anti-GNA33 Antibodies to the Bacterial Cell Surface as Determined by Indirect Fluorescence Flow Cytometry CD1 mice were immunized with rGNA33 (encoded by the gene from strain 2996). The resulting polyclonal antibody-containing antisera were tested for their ability to bind to live bacterial cells of various MenB strains as determined by a flow cytometric detection of indirect immunofluorescence binding assay. FIG. 1A shows binding of polyclonal anti-rGNA33 antisera to four representative MenB strains, the parent strain 2996 (P1.5,2), and three other strains M3735 (P1.5,2), M4207 (P1.5) and MC58 (P1.7,16). The anti-GNA33 polyclonal antiserum reacted only with strains 2996 and M3735. The anti-capsular positive control mAb bound to all four strains, whereas the negative control antiserum prepared from animals immunized with *E. coli* proteins, showed only background binding. FIG. 1B shows the results of similar experiments measuring binding of the anti-GNA33 mAb 25 to the bacterial cell surface of three strains (M3735 (P1.5, 2), M4207 (P1.5) and MC58 (P1.7,16). The mAb bound only to strain M3735 (P1.5,2).

Table 1 summarizes the results of flow cytometry experiments measuring the ability of anti-GNA33 antibody or mAb 25 to bind to the surface of live bacteria from 22 genetically diverse encapsulated meningococcal strains (21 serogroup B and 1 serogroup C). The anti-GNA33 antibody bound only to strains with the P1.5,2 or P1.2 serosubtypes (9 of 9 vs. 0 of 13 strains with other PorA serosubtypes; P<0.001). One of the nine positive strains, M986, showed lower binding than the other eight strains (vide infra). There was no binding to three strains (M4207, 1000, and BZ83) that express the P1.5 epitope (present on loop 1 of PorA, Sacchi et al., *Infect. Dis*. (2000) 182:1169-1176) but not the P1.2 epitope (loop 4).

Also, there was no binding to strain M136, which does not express PorA (i.e. P1-). These data indicate that binding of anti-GNA33 antibody to the bacterial surface correlates with expression of the PorA serosubtype P1.2.

EXAMPLE 2

Western Blot of Total Membrane Fractions Prepared from Different *N. meningitidis* Group B Strains The apparent association between binding of anti-GNA33 antibody to the bacterial surface and the P1.2 serosubtype was unexpected and investigated further by Western blot of total protein prepared from representative strains and resolved by SDS-PAGE. Results from four serogroup B strains, two that were negative for anti-GNA33 surface binding by flow cytometry, NG3/88 (P1.7,1) and MC58 (P1.17,16), and two that were positive, BZ232 and NMB (both P1.5,2), are shown in FIG. 2. Data also are shown for total membrane preparations from three strains (MC58, BZ232 and NMB) in which the genes encoding GNA33 had been inactivated.

In FIG. 2A, a single band with an apparent mass of approximately 48 kDa was detected by the anti-GNA33 mAb 25 in membrane preparations from the two non-P1.2 strains, NG3/88 (lane 3) and MC58 (lane 4). The band has an apparent molecular mass expected for rGNA33 (lane 1), and was absent in total protein prepared from the control *E. coli* strain (lane 2), and from the GNA33 knockout in strain MC58 (lane 5). Lanes 6 and 8 contain total proteins prepared from strains BZ232 and NMB, respectively. Both of these strains have the PorA serosubtype P1.5,2. In each of the lanes there are two anti-GNA33-reactive bands. The higher 48 kDa band is absent from the GNA33 knockouts derived from BZ232 and NMB (lanes 7 and 9, respectively), a result confirming that this protein is GNA33. The lower molecular mass anti-GNA33-reactive bands appear to be PorA based on reactivity with a mAb reactive with P1.2 (see FIG. 2B).

FIG. 2B shows a Western blot of the same protein samples as described for FIG. 2A but using the anti-PorA P1.2 mAb as the primary detecting antibody. As expected, there was no reactivity of the anti-PorA mAb with rGNA33 (lane 1), the negative control *E. coli* proteins (lane 2), or with total membranes prepared from strains that do not express PorA P1.2 (lanes 3, 4 and 5). However, a protein having an apparent mass expected for PorA was detected in total membrane preparations from strains BZ232 (lane 6), BZ232ΔGNA33 (lane 7), NMB (lane 8) and NMBΔGNA33 (lane 9), that express PorA P1.2. This protein also is present in preparations from their respective GNA33 knockouts (lanes 7 and 9, respectively). These results confirm that the protein with an apparent mass of 41 kDa reacting with the anti-GNA33 mAb in FIG. 2A was PorA. In contrast, the anti-PorA P1.2 mAb did not react by Western blot with GNA33.

EXAMPLE 3

Peptide Mapping of the Surface-Exposed PorA Epitope Recognized by the Anti-GNA33 mAb 25

The anti-P1.2 mAb is known to recognize an epitope on PorA present on loop 4. Table 2 shows a comparison of the loop 4 variable region (VR$_2$) amino acid sequences for selected MenB strains included in the present study (see Sacchi et al., *Infect. Dis*. (2000) 182:1169-1176, or the URL address: http file type, mlst host server, domain name zoo.ox.ac.uk, file Meninagcoccus directory for recently revised PorA VR designation conventions). Included in Table 2 are the sequences of two closely related VR₂ types, P1.10 and P1.10-1 from BZ83 (P1.10) and M4207 (P1.10-1), respectively, which were negative for surface binding by the anti-GNA33 mAb. The loop 4 sequences of the two negative strains differ from the anti-GNA33 positive strains by a six amino acid peptide. The positive P1.2 strains contain the hexapeptide QTPKSQ (SEQ ID NO:16) or QTPQSQ (SEQ ID NO:17), whereas the negative P1.10 or P1.10-1 strains contain the hexapeptide NKQNQR (SEQ ID NO:18) or NKQNQP (SEQ ID NO:19), respectively (Table 2).

In particular, to identify the specific amino acid sequence recognized by Anti-GNA33 mAb 25, overlapping linear decapeptides spanning the entire amino acid sequences of GNA33 (Table 3), and of loop 4 of PorA (P1.2-2 from strain 2996), GenBank accession number X57180, were synthesized [Note: The sequence given in X57180 encodes a VR₂ having the sequence QTPE (SEQ ID NO:20). However, this sequence has subsequently be found to be in error (C. T. Sacchi, CDC, Atlanta, Ga., personal communication). The correct sequence is QTPQ (SEQ ID NO:21).]. The peptides that were positive≧8 dye units) with mAb 25 are detailed in Table 3. All eight of the positive GNA33 peptides share a tripeptide, QTP. The QTP sequence is also present in all five positive PorA P1.2 peptides that reacted with mAb 25. However, the QTP sequence is not sufficient for anti-GNA33 binding as there was no mAb binding to three loop 4 peptides that contained QTP but lacked the preceding FVQ sequence.

Figure 4B:
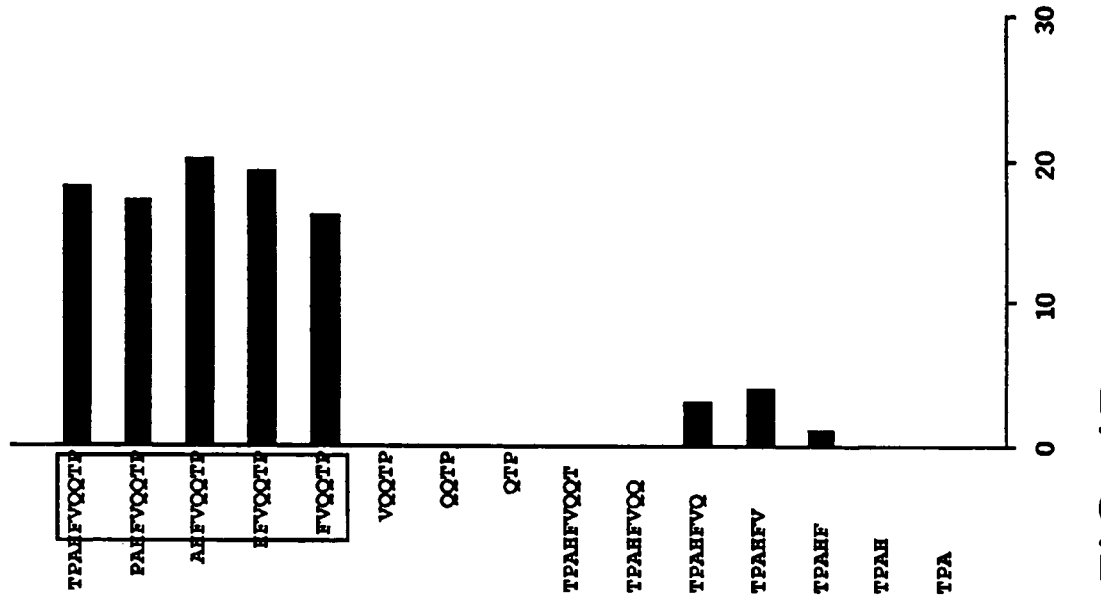
FIG. 4B, TPAHFVQQTP (SEQ ID NO:22), PAHFVQQTP (amino acids 1-9 of SEQ ID NO:38), AHFVQQTP (amino acids 3-10 of SEQ ID NO:22), HFVQQTP (amino acids 4-10 of SEQ ID NO:22), FVQQTP (amino acids 5-10 of SEQ ID NO:22) VQQTP (amino acids 6-10 of SEQ ID NO:22), QQTP (amino acids 7-10 of SEQ ID NO:22), TPAHFVQQT (amino acids 1-9 of SEQ ID NO:22), TPAHFVQQ (amino acids 1-8 of SEQ ID NO:22), TPAHFVQ (amino acids 1-7 of SEQ ID NO:22), TPAHFV (amino acids 1-6 of SEQ ID NO:22), TPAHF (amino acids 1-5 of SEQ ID NO:22), TPAH (amino acids 1-4 of SEQ ID NO:22).
Figure 4A:
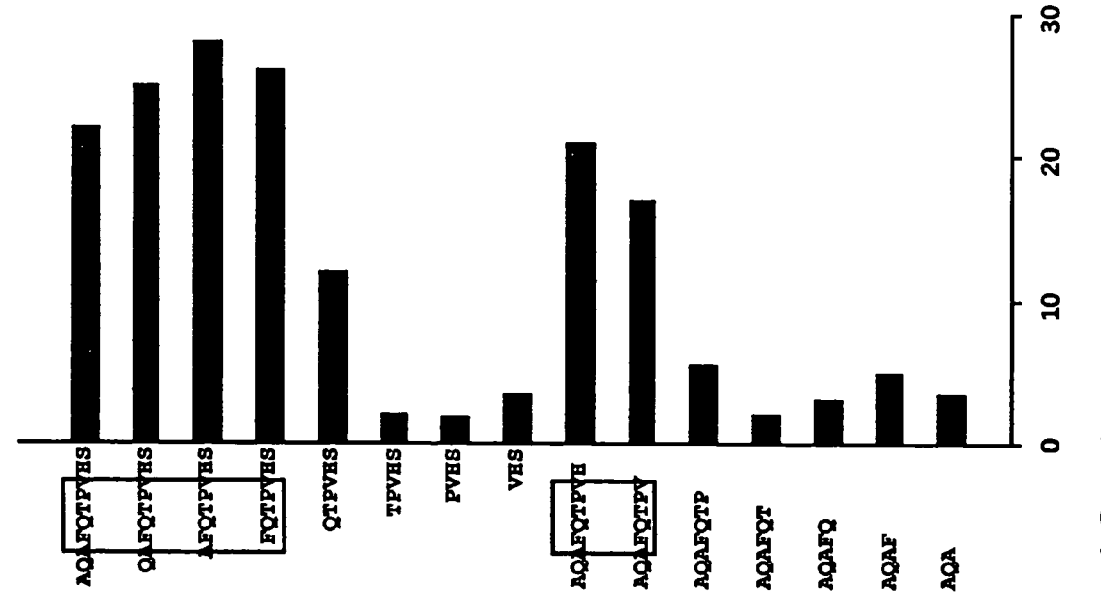
FIG. 4A, AQAFQTPVHS (SEQ ID NO:6), QAFQTPVHS (SEQ ID NO:5), AFQTPVHS (SEQ ID NO:4), FQTPVHS (SEQ ID NO:3), QTPVHS (amino acids 5-10 of SEQ ID NO:6), TPVHS (amino acids 6-10 of SEQ ID NO:6), PVHS (amino acids 7-10 of SEQ ID NO:6), AQAFQTPVH (SEQ ID NO:7), AQAFQTPV (SEQ ID NO:8), AQAFQTP (amino acids 1-7 of SEQ ID NO:7), AQAFQT (amino acids 1-6 of SEQ ID NO:7), AQAFQ (amino acids 1-5 of SEQ ID NO:7), AQAF (amino acids 1-4 of SEQ ID NO:7).

To define the minimal peptide sequence from each protein that is sufficient for anti-GNA mAb 25 binding, progressively smaller peptides were synthesized beginning with AQAFQT-PVHS (FIG. 4A; SEQ ID NO:6), and PorA P1.2 peptides beginning with TPAHFVQQTP (FIG. 4B; SEQ ID NO:22). The mAb bound strongly with GNA33 peptides containing FQTPV (SEQ ID NO:2), and PorA P1.2 peptides containing FVQQTP (SEQ ID NO:23), but not with any of the smaller peptides. The same minimal epitopes for each protein were identified by systematic alanine or glycine substitutions of amino acids contained within the relevant peptides of loop 4 of PorA and the GNA33. See Table 4 for a summary of the alanine substitution data for PorA loop 4 VR type P1.2-2.

These data suggest that the antibodies elicited by rGNA33 have bactericidal activity against Nm strains expressing the P1.2 epitope as the result of cross-reactivity with the P1.2 epitope of PorA that contains the sequence QTP.

EXAMPLE 4

Figure 5A:
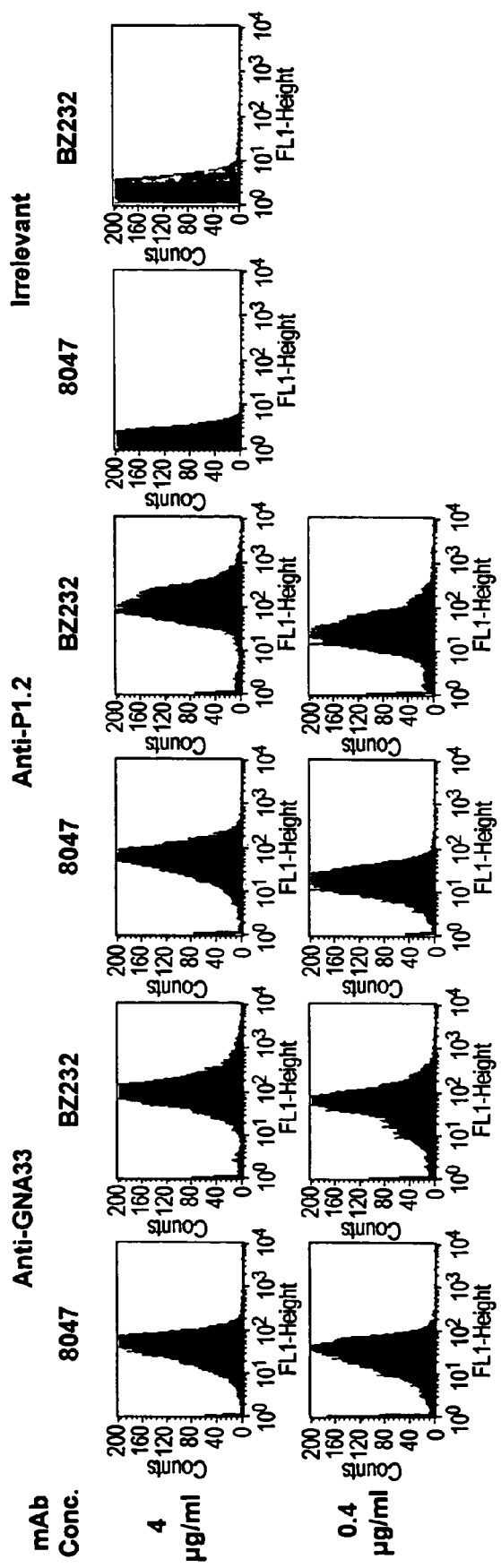
FIGS. 5A-5B show binding of murine mAbs to live encapsulated NmB strains as determined by indirect fluorescence flow cytometry. The mAbs tested are described in legend to FIG. 1B.
Figure 5B:
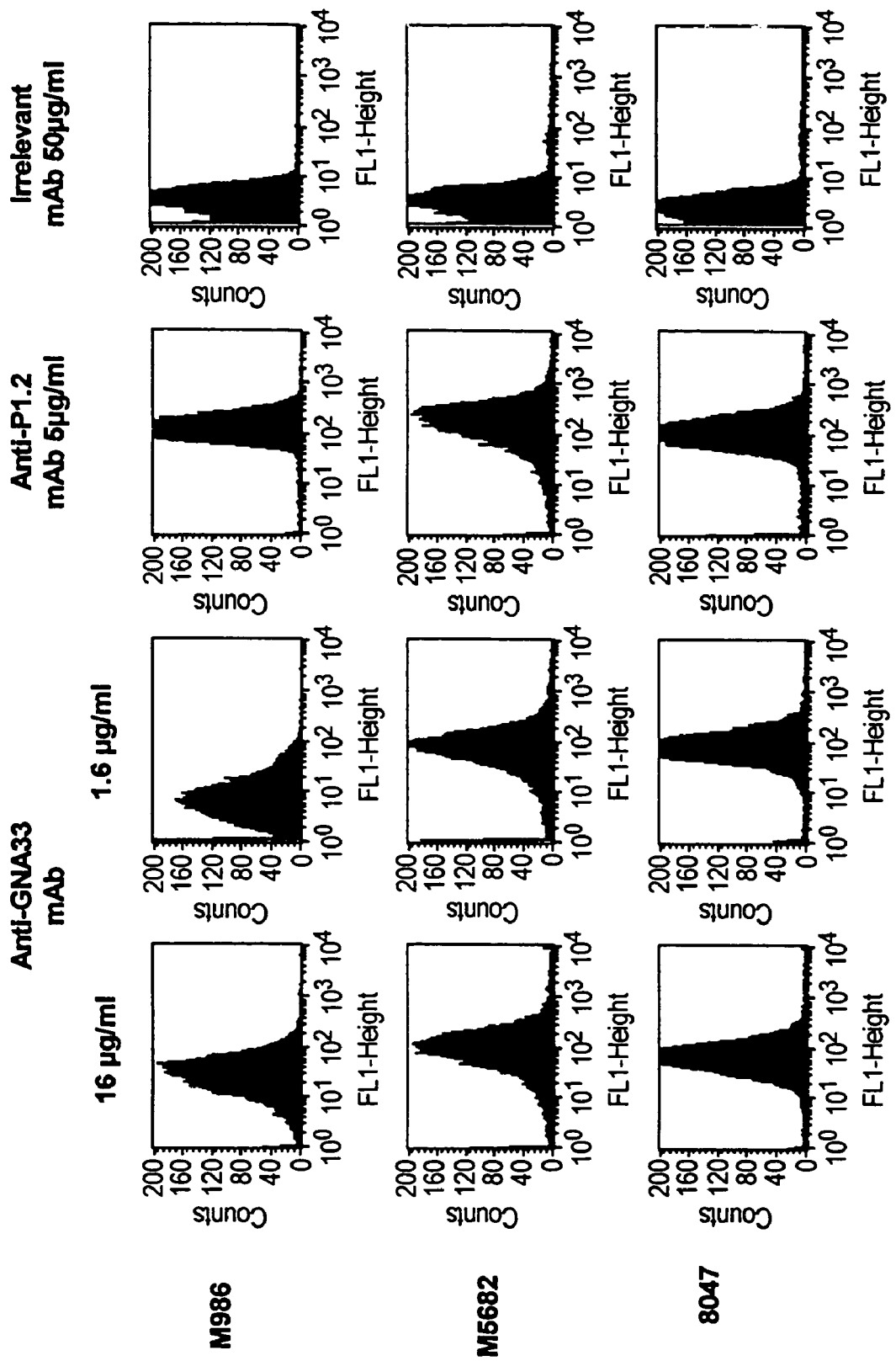

Comparative Binding of Anti-GNA33 and Anti-PorA P1.2 Antibodies to P1.2 NmB Strains The unexpected finding that anti-rGNA33 antibodies cross-react with the PorA P1.2 epitope provided an opportunity to compare the activity of antibody raised to rGNA33 with that elicited by PorA serosubtype P1.2. With one exception, the concentration-dependent binding of the anti-GNA33 mAb was similar to that of a control anti-PorA P1.2 mAb for the nine P1.2 strains tested (see representative data for strains 8047 and BZ232 in FIG. 5A). The exception, strain M986, showed relatively weaker anti-GNA33 antibody binding when compared with binding to the other P1.2 strains (FIG. 5B). In contrast, binding by the anti-PorA P1.2 mAb was similar for all P1.2 strains including M986.

The VR₂ sequence type of strain M986 is reported to be P1.2 (GenBank accession number U92912), which is defined by a loop 4 sequence that includes the segment FVQQTPK (SEQ ID NO:24), as opposed to FVQQTPQ (SEQ ID NO:25) for strains 8047 and BZ232 (VR₂ type P1.2-2; Table 1). The VR₂ type is based on the amino acid sequence of the particular P1.2 epitope. Two other strains reported to have VR₂ sequence type P1.2 (strains M3735 and M5682) showed strong anti-GNA33 antibody binding which, in each strain, was comparable to the respective binding of the control anti-PorA P1.2 mAb (see for example, binding data with stain M3735, FIG. 1A and M5682, FIG. 5B). The VR₂ sequence type of PorA loop 4 in M986, M3735, and M5682 was confirmed to be P1.2 by nucleotide sequencing a second time. Therefore, the sequence difference (K to Q) does not appear to be sufficient to explain the decreased anti-GNA33 binding activity with strain M986.

EXAMPLE 5

Bactericidal Activity

The complement-dependent bactericidal activity of murine mAbs to PorA P1.2, rGNA33 (mAb 25), and serogroup B (SEAM 12) and C (mAb 181.1) polysaccharide capsules were compared. With the exception of the serogroup C anticapsular mAb (subclass IgG3) that was used to test NmC strain M5954, the subclass of all of the other mAbs was IgG2a. The $BC_{50}$ of the anti-PorA P1.2 mAb in the presence of human complement was <0.5 µg/ml for all nine strains. The corresponding $BC_{50}$ values of the serogroup B anticapsular mAb were higher, ranging between 5 to 12 µg/ml, and for the serogroup C mAb (strain M5954), <1 µg/ml. As summarized in Table 5, the bactericidal activity of the anti-GNA33 mAb was variable and was dependent on the complement source used. For three of the strains (8047, NMB and M3735), $BC_{50}$ values of the anti-GNA33 mAb in the presence of human complement ranged from 7 to 15 µg/ml. The values for these strains were similar to those of the anticapsular antibody. For the remaining six strains (2996, BZ232, M5545, M5682, M5954, and M986), there was no killing observed with the anti-GNA33 mAb in the presence of human complement ($BC_{50}$>60 µg/ml when tested with serum from a normal adult with no endogenous bactericidal activity (Table 5), and >30 µg/ml when tested with serum from a patient with agammaglobulinemia). When infant rabbit serum was used as the complement source, all but one of the six strains were susceptible to anti-GNA33-induced lysis. The $BC_{50}$ values of the susceptible strains ranged from ≦1 µg/ml to 8 µg/ml (Table 5). Again, the exception was strain M986, where no killing was observed with the anti-GNA33 mAb when tested with human or rabbit complement ($BC_{50}$ values >150 and >30 µg/ml, respectively). Lack of bacteriolysis for this strain may be related to the lower surface binding of the mAb as measured by flow cytometry (FIG. 5B). The respective bactericidal titers of polyclonal mouse anti-rGNA33 antiserum with human complement against the five strains tested corresponded to the results measured with anti-GNA33 mAb 25 (Table 5).

EXAMPLE 6

Passive Protection by Anti-GNA33 Antisera

The ability of polyclonal mouse anti-GNA33 antibody to confer passive protection against MenB bacteremia was assessed in an infant rat model. Three strains were used: 8047, a strain susceptible to anti-GNA33 bacteriolysis in the presence of human or rabbit complement; BZ232, a strain resistant to anti-GNA33 bacteriolysis with human complement but susceptible with rabbit or rat complement; and M986, a strain resistant to anti-GNA33 bacteriolysis in the presence of human, rabbit or rat complement. The results of testing passive protection in this model are summarized in Table 6.

In experiment 1, 100 μl of a 1:5 or 1:25 dilution of polyclonal mouse anti-GNA33 antisera mixed with 5.8×10³ CFU of strain 8047 and given i.p. completely protected rats against bacteremia measured 18 hours after the challenge. In the same experiment, all animals given 100 μl of a 1:5 or 1:25 dilution of the anti-GNA33 antisera mixed with 6.5×10³ CFU of strain M986, a strain resistant to anti-GNA33 bacteriolysis, developed bacteremia. Despite lack of bactericidal activity, the geometric mean CFU/ml of blood of the animals treated with the anti-GNA antisera and challenged with strain M986 was 10- to 20-fold lower than that of control animals treated with a negative control antiserum prepared against *E. coli* proteins (P=0.02). Similar results were obtained in a second experiment (experiment 2) with anti-GNA33 mAb 25. All six rats pretreated with 20 μg of mAb 25, i.p., at time 0 and challenged 2 hours later with 3.5×10³ CFU of strain M986 had bacteria present in blood samples obtained 18 hours after challenge. However, the geometric mean CFU/ml was less than 0.3% of that of control animals pre-treated with an irrelevant mAb (P<0.02). In the same experiment, 20 μg per rat of the anti-P1.2 mAb was completely protective against strain M986, and 2 μg per rat was partially protective (only 1 of 6 treated animals developed bactermia).

In third and fourth (experiments 3 and 4), rats were challenged with strain BZ232 (resistant to anti-GNA33 bacteriolysis with human complement but susceptible with rabbit or rat complement). In this experiment, the protective activity of the anti-GNA33 mAb against this strain was similar or higher than that of the control anticapsular antibody, and only slightly less than that of the anti-PorA P1.2 mAb.

As shown above, mouse antibodies produced as the result of immunization with rGNA33 are able to mediate bacteriolysis of *N. meningitidis* strains in the presence of complement because of cross-reactivity of anti-GNA33 antibodies with the P1.2 epitope of the porin protein, PorA. This result was unexpected since GNA33 and PorA have no significant sequence homology, are structurally and functionally unrelated, and are physically located in different bacterial substructures. Hence, GNA33 can be described as an immunologic mimic of PorA.

The molecular mimicry exhibited by GNA33 is exceptional. First, GNA33 is a non-immunoglobulin protein that, as described above, is unrelated to PorA. Second, rGNA33 elicits an antibody response that, in many respects, is similar in functional activity to that elicited by native PorA in outer membrane vesicle preparations. Third, the polyclonal mouse anti-rGNA33 antisera described here were prepared in two independent laboratories and the bactericidal data were independently replicated.

In previous studies, immunization with peptides corresponding to loop 4 of PorA P1.2 failed to elicit antibodies that bound to the native protein, or mediated bacteriolysis in the presence of complement (McGuinness et al., *J. Exp. Med.* (1990) 171:1871-1872). Presumably, the smaller peptide fragments were unable to adopt stable conformations present in native porin. Similarly, immunization with rPorA expressed in *E. coli* or *B. subtilus*, failed to elicit bactericidal antibody unless the conformation of the surface-accessible PorA epitopes in the recombinant protein were reconstituted using liposomes or detergents (Christodoulides et al., *Microbiology* (1998) 144:3027-3037 and Idänpään-Heikkila et al., *Vaccine* (1995) 13:1501-1508. These results suggest that the epitopes on PorA responsible for eliciting bactericidal antibody are conformational. In contrast, as shown herein, immunization with the rGNA33 mimetic elicited bactericidal antibody that cross-reacted with the P1.2 epitope of PorA loop 4. Unlike rPorA, this occurred when the recombinant GNA33 protein used as the immunogen was simply mixed with Freund's adjuvant, without the need for renaturation of the recombinant molecule.

Thus, GNA33 polypeptides, epitopes, antibodies directed against the same and uses of these molecules are described. From the foregoing, it will be appreciated that, although specific embodiments of the invention have been described herein for purposes of illustration, various modifications may be made without deviating from the spirit and scope defined by the appended claims.

TABLE 1

Binding of anti-GNA33 antibodies to the surface of live, encapsulated *N. meningitidis* strains as measured by flow cytometry in relation to serological classification and PorA VR designation.

| Nm strain | Country | Year | Serologic classification[A] | PorA VR designation (sequence)[B] | Anti-GNA33[C] |
|---|---|---|---|---|---|
| M5954 | U.S. | 1997 | C:2a:P1.2 | ND | + |
| M5682 | U.S. | 1999 | B:2a:P1.5,2 | P1.5,2 | + |
| M986 | U.S. | 1963 | B:2a:P1.5,2 | P1.5,2 | + |
| M3735 | U.S. | 1992 | B:NT:P1.5,2 | P1.5-1,2 | + |
| M5545 | U.S. | 1998 | B:NT:P1.5,2 | P1.5-4,2-2 | + |
| 8047 | U.S. | 1978 | B:2b:P1.5,2 | P1.5-2,2-2 | + |
| NMB | U.S. | 1982 | B:2b:P1.5,2 | P1.5-2,2-2 | + |
| BZ232 | Netherlands | 1964 | B:NT:P1.2 | P1.5-2,2-2 | + |
| 2996 | Netherlands | 1975 | B:2b:P1.5,2 | P1.5-1,2-2 | + |
| M136 | U.S. | 1968 | B:16,11:P1- | P1.5-1,2-2 | − |
| M4207 | U.S. | 1997 | B:10:P1.5 | P1.5-1,10-1[C] | − |
| 1000 | USSR | 1989 | B:NT:P1.5 | P1.5-1,10-4 | − |
| BZ83 | Netherlands | 1984 | B:P1.5,10 | P1.5-1,10 | − |
| NG6/88 | Norway | 1988 | B:NT:P1.1 | P1.7-4,1 | − |
| BZ198 | Netherlands | 1986 | B:NT:P.NST | P1.7-4,4 | − |
| S3446 | U.S. | 1972 | B:19,14:P1.22, 14 | P1.22-1,14 | − |
| IH5341 | Finland | 1985 | B:15:P1.7,16 | ND | − |
| CU385 | Cuba | 1980 | B:4,7:P1.19,15 | P1.19,15 | − |
| SWZ107 | Switzerland | 1980 | B:4:P.NST | P1.22-1,14 | − |
| H44/76 | Norway | 1976 | B:15:P1.7, 16 | P1.7,16 | − |
| NG3/88 | Norway | 1988 | B:8:P1.7,1 | P1.7,1 | − |
| MC58 | U.K. | 1985 | B:15:P1.7,16 | 15:P1.7,16-2 | − |

[A]NST = non-serosubtypable with available mAbs; − = PorA expression not detectable by SDS-PAGE.
[B]Based on the revised PorA VR type designation nomenclature proposed by Sacchi et al., Infect. Dis. (2000) 182:1169-1176 and the URL address: http file type, www host server, domain name Neisseria.mist.net.
[C]Measured with mouse polyclonal anti-GNA33 antisera and/or mAB 25.

TABLE 2

Binding of Anti-GNA33 Antibody to the Cell Surface of Different MenB Strains

| Strain | VR2 Sequence Type | PorA Loop 4 Amino Acid Sequence | Surface Binding |
|---|---|---|---|
| M3735 | P1.2 | HFVQ QTPKSQ PTLVP (SEQ ID NO: 32) | Pos |
| BZ232 | P1.2-2 | HFVQ QTPQSQ PTLVP (SEQ ID NO: 33) | Pos |
| 2996 | P1.2-2 | HFVQ QTPQSQ PTLVP (SEQ ID NO: 33) | Pos |
| BZ83 | P1.10 | HFVQ NKQNQR PTLVP (SEQ ID NO: 34) | Neg |
| M4207 | P1.10-1 | HFVQ NKQNQP PTLVP (SEQ ID NO: 34) | Neg |

TABLE 3

Epitope mapping of anti-GNA33 mAb 25 against overlapping peptides prepared from GNA33 and loop 4 of PorA P1.2 (strain 2996)

| GNA33[A] | Dye Units | Loop 4 of PorA P1.2[A] | Dye Units |
|---|---|---|---|
| QDVSAQAFQT (SEQ ID NO: 35) | 0 | YTPAHFVQQT (SEQ ID NO: 37) | 0 |
| DVSAQAFQTP [(SEQ ID NO: 12)] | 23 | TPAHFVQQTP (SEQ ID NO: 22) | 8 |
| VSAQAFQTPV (SEQ ID NO: 13) | 27 | PAHFVQQTPQ (SEQ ID NO: 38) | 10 |
| SAQAFQTPVH (SEQ ID NO: 14) | 29 | AHFVQQTPQS (SEQ ID NO: 15) | 14 |
| AQAFQTPVHS (SEQ ID NO: 6) | 30 | HFVQQTPQSQ (SEQ ID NO: 39) | 15 |
| QAFQTPVHSF (SEQ ID NO: 9) | 30 | FVQQTPQSQP (SEQ ID NO: 40) | 9 |
| AFQTPVHSFQ (SEQ ID NO: 10) | 24 | VQQTPQSQPT (SEQ ID NO: 41) | 4 |
| FQTPVHSFQA (SEQ ID NO: 11) | 22 | QQTPQSQPTL (SEQ ID NO: 42) | 0 |
| QTPVHSFQAK (SEQ ID NO: 12) | 19 | QTPQSQPTLV (SEQ ID NO: 43) | 2 |
| TPVHSFQAKQ (SEQ ID NO: 36) | 2 | TPQSQPTVP (SEQ ID NO: 44) | 2 |

[A]The peptide sequences were considered positive for binding to the anti-GNA33 mAb if the developed spots were = 10 dye units.

TABLE 4

Effect of Alanine Substitution on Binding of Anti-GNA33 mAb 25

| 10-mer Peptide | Relative Binding | | |
|---|---|---|---|
| PGH FVQ QTP Q (SEQ ID NO: 45) | 8 | | |
| PAA FVQ QTP Q (SEQ ID NO: 46) | 8 | Consensus Peptide | |
| PAH AVQ QTP Q (SEQ ID NO: 47) | 1 | FVQQTPA (SEQ ID NO: 54) | |
| PAH FAQ QTP Q (SEQ ID NO: 48) | 4 | | |
| PAH FVA QTP Q (SEQ ID NO: 49) | 2 | | |
| PAH FVQ ATP Q (SEQ ID NO: 50) | 0 | | |
| PAH FVQ QAP Q (SEQ ID NO: 51) | 0 | | |
| PAH FVQ QTA Q (SEQ ID NO: 52) | 0 | | |
| PAK FVQ QTP A (SEQ ID NO: 53) | 2 | | |

TABLE 5

Bactericidal activity of anti-GNA33 antibodies against different Nm Strains

| Strain | VR2 sequence type | Polyclonal antisera $BC_{50}$ (1/titer)[A] Human complement[B,C] | mAb 25 $BC_{50}$ (μg/ml)[A] Human complement[B] | Rabbit complement |
|---|---|---|---|---|
| 8047 | P1.2-2 | =>16 | 15 | <0.5 |
| NMB | P1.2-2 | =>16 | 9 | ND[C] |
| M3735 | P1.2 | ND | 7 | ND |
| 2996 | P1.2-2 | <4 | >60 | <0.5 |
| BZ232 | P1.2-2 | <4 | >150 | <0.5 |
| M5682 | P1.2 | ND | >60 | <0.5 |
| M5954 | P1.2 | ND | >60 | 1 |
| M5545 | P1.2 | ND | >60 | 8 |
| M986 | P1.2 | <4 | >150 | >30 |

[A]$BC_{50}$, concentration of mAb, or reciprocal dilution of antiserum that when incubated for 60 min with bacterial cells and 20% complement yielded a 50% decrease in CFU per ml compared to that at time zero.
[B]The $BC_{50}$ values of the anti-PorA P1.2 mAb with human complement ranged from = 0.25 μg/ml to 0.5 μg/ml. The $BC_{50}$ of the serogroup B anti-capsular mAb (SEAM 12) with human complement for the eight serogroup B strains ranged from 5 μg/ml to 15 μg/ml. The $BC_{50}$ for the serogroup C anticapsular mAb (181.1) for strain M5954 with human complement was <1 μg/ml.
[C]ND, not done.

TABLE 6

Anti-GNA33 antibody passive protection in infant rats challenged with N. meningitidis serogroup B strains 8047, M986, or BZ232

| Experiment | Strain (challenge CFU per rat) | Treatment[A] | Serum Dilution or dose | Blood culture at 18 hrs No. positive/ Total | CFU/ml (geo. mean, $10^3$)[B] |
|---|---|---|---|---|---|
| 1 | 8047 ($5.8 \times 10^3$) | Anticapsular mAb | 2 | 0/5 | <0.001 |
| | | Anti-GNA33 antiserum | 1:5 | 0/5 | <0.001 |
| | | Anti-GNA33 antiserum | 1:25 | 0/5 | <0.001 |
| | | Anti-E. coli antiserum | 1:5 | 5/5 | 53 |
| | | Irrelevant mAb | 2 | 5/5 | 63 |
| 1 | M986 ($6.5 \times 10^3$) | Anticapsular mAb | 2 | 0/5 | <0.001 |
| | | Anti-GNA33 antiserum | 1:5 | 5/5 | 19 |
| | | Anti-GNA33 antiserum | 1:25 | 5/5 | 41 |
| | | Anti-E. coli antiserum | 1:5 | 5/5 | 408 |
| | | Irrelevant mAb | 2 | 5/5 | 203 |
| 2 | M986 ($3.5 \times 10^3$) | Anticapsular mAb | 20 | 1/6 | 0.002 |
| | | Anti-GNA33 mAb | 20 | 6/6 | 1.873 |

TABLE 6-continued

Anti-GNA33 antibody passive protection in infant rats challenged with *N. meningitidis* serogroup B strains 8047, M986, or BZ232

| Experiment | Strain (challenge CFU per rat) | Treatment[A] | Serum Dilution or dose | Blood culture at 18 hrs No. positive/ Total | CFU/ml (geo. mean, $10^3$)[B] |
|---|---|---|---|---|---|
| | | Anti-PorA P1.2 mAb | 20 | 0/6 | <0.001 |
| | | Anti-PorA P1.2 mAb | 2 | 1/6 | 0.003 |
| | | Irrelevant mAb | 20 | 6/6 | 630 |
| 3 | BZ232 | Anticapsular mAb | 10 | 3/6 | <0.056 |
| | ($7.1 \times 10^3$) | Anti-GNA33 mAb | 15 | 0/6 | <0.001 |
| | | Anti-GNA33 mAb | 3 | 1/6 | <0.006 |
| | | Anti-GNA33 mAb | 0.6 | 5/6 | 0.282 |
| | | Anti-PorA P1.2 mAb | 15 | 0/6 | <0.001 |
| | | Anti-PorA P1.2 mAb | 3 | 0/6 | 0.001 |
| | | Irrelevant mAb | 15 | 6/6 | >500. |
| 4 | BZ232 | Anti-GNA33 mAb | 0.6 | 5/6 | 4.562 |
| | ($4.7 \times 10^3$) | Anti-PorA P1.2 | 3.0 | 0/6 | <0.001 |
| | | Anti-PorA P1.2 | 0.6 | 0/6 | <0.001 |
| | | Anti-PorA P1.2 | 0.12 | 3/7 | 0.022 |
| | | Irrelevant mAb | 3 | 8/8 | 273 |

[A]In experiment 1, bacteria were mixed together with antisera or control mAb immediately before the i.p. challenge. In experiment 2, 3, and 4, animals were treated i.p with the mAb at time 0. Two hours later they were challenged i.p with the bacteria. In both experiments, blood cultures were obtained 18 hours after the challenge.
[B]For calculation of geometric mean CFU/ml, animals with sterile cultures were assigned a value of 1 CFU/ml. In experiment 1, the geometric mean CFU/ml of the combined group of animals given a 1:5 or 1:25 dilution of anti-GNA33 antisera and challenged with strain M986 ($28.8 \times 10^3$) was lower than that of the combined group of controls given the irrelevant mAb or *E. coli* antiserum ($350 \times 10^3$, P = .02). In experiments 2, 3, and 4, the geometric mean CFU/ml of the animals treated with the anti-GNA33 mAb was lower than that of controls given the irrelevant mAb (P < .02).

The invention claimed is:

1. An isolated GNA33 peptide which is less than a full-length GNA33 protein of a *Neisseria meningitidis* serogroup B bacterium and which comprises an amino acid sequence selected from the group consisting of DVSAQAFQTP (SEQ ID NO: 55), VSAQAFQTPV (SEQ ID NO: 13) and SAQAFQTPVH (SEQ ID NO: 14), wherein said peptide binds to an anti-GNA33 antibody that exhibits complement-mediated bactericidal activity against a *Neisseria meningitidis* serogroup B subserotype P1.2 bacterium.

2. A composition comprising the GNA33 peptide of claim 1 and a pharmaceutically acceptable excipient.

3. The isolated GNA33 peptide of claim 1 which comprises between 1 and 50 amino acids at the N terminus of the amino acid sequence.

4. The isolated GNA33 peptide of claim 1 which comprises between 1 and 50 amino acids at the C terminus of the amino acid sequence.

5. The isolated GNA33 peptide of claim 1 which comprises more than 50 amino acids at the N terminus of the amino acid sequence.

6. The isolated GNA33 peptide of claim 1 which comprises more than 50 amino acids at the C terminus of the amino acid sequence.

7. The isolated GNA33 peptide of claim 1 which comprises between 1 and 3 amino acids at the N terminus of the amino acid sequence.

8. The isolated GNA33 peptide of claim 1 which comprises between 1 and 3 amino acids at the C terminus of the amino acid sequence.

9. The isolated GNA33 peptide of claim 1 which comprises between 1 and 5 amino acids at the N terminus of the amino acid sequence.

10. The isolated GNA33 peptide of claim 1 which comprises between 1 and 5 amino acids at the C terminus of the amino acid sequence.

11. The isolated GNA33 peptide of claim 1 which comprises between 1 and 10 amino acids at the N terminus of the amino acid sequence.

12. The isolated GNA33 peptide of claim 1 which comprises between 1 and 10 amino acids at the C terminus of the amino acid sequence.

13. The isolated GNA33 peptide of claim 1 which comprises between 1 and 25 amino acids at the N terminus of the amino acid sequence.

14. The isolated GNA33 peptide of claim 1 which comprises between 1 and 25 amino acids at the C terminus of the amino acid sequence.

15. The isolated GNA33 peptide of claim 1 wherein the peptide contains only 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 additional amino acids at the N terminus of the amino acid sequence.

16. The isolated GNA33 peptide of claim 1 wherein the peptide contains only 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 additional amino acids at the C terminus of the amino acid sequence.

17. An isolated GNA33 peptide consisting of the amino acid sequence FQTPV (SEQ ID NO:2), AFQTPVHSFQ (SEQ ID NO:10), FQTPVHSFQA (SEQ ID NO: 11), QTPVHSFQAK (SEQ ID NO: 12), DVSAQAFQTP (SEQ ID NO:55), VSAQAFQTPV (SEQ ID NO: 13), or SAQAFQTPVH (SEQ ID NO: 14).

18. A method of eliciting an immune response against a *Neisseria meningitidis* serogroup B bacterium in a mammalian subject comprising administering an effective amount of the composition of claim 2 to the subject.

* * * * *

UNITED STATES PATENT AND TRADEMARK OFFICE
CERTIFICATE OF CORRECTION

| | | |
|---|---|---|
| PATENT NO. | : 7,534,444 B2 | Page 1 of 1 |
| APPLICATION NO. | : 10/121456 | |
| DATED | : May 19, 2009 | |
| INVENTOR(S) | : Dan M. Granoff, Gregory Moe and Rino Rappuoli | |

It is certified that error appears in the above-identified patent and that said Letters Patent is hereby corrected as shown below:

On the Title Page:

Item (73) should read: Assignee: Novartis Vaccines and Diagnostics, Inc., Emeryville, CA (US) and Children's Hospital & Research Center Oakland, Oakland, CA (US)

Signed and Sealed this
Eighth Day of February, 2011

David J. Kappos
*Director of the United States Patent and Trademark Office*